United States Patent
Frank et al.

(10) Patent No.: US 6,841,127 B2
(45) Date of Patent: *Jan. 11, 2005

(54) IN-SITU INJECTION AND MATERIALS SCREENING DEVICE

(75) Inventors: Trevor G. Frank, Fremont, CA (US); Keith A. Hall, San Jose, CA (US); William H. Chandler, Jr., Milpitas, CA (US); Thomas Boussie, Menlo Park, CA (US); Thomas J. Crevier, San Jose, CA (US); Leonid Matsiev, San Jose, CA (US); Christopher Goh, San Francisco, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 43 days.

This patent is subject to a terminal disclaimer.

(21) Appl. No.: 10/187,406

(22) Filed: Jun. 28, 2002

(65) Prior Publication Data

US 2003/0045000 A1 Mar. 6, 2003

Related U.S. Application Data

(63) Continuation-in-part of application No. 09/895,945, filed on Jun. 29, 2001.

(51) Int. Cl.[7] .................. G01N 33/48; G01N 21/00; G01N 31/00; G01N 33/00; G01N 15/06
(52) U.S. Cl. .................. 422/68.1; 422/50; 422/62; 422/63; 422/64; 422/65; 422/67; 422/82.05; 422/82.08; 436/8; 436/43; 436/44; 436/47; 436/48; 436/164; 436/174
(58) Field of Search .................. 422/50, 62, 63, 422/64, 65, 67, 68.1, 82.05, 82.08; 436/8, 43, 44, 47, 48, 164, 174

(56) References Cited

U.S. PATENT DOCUMENTS

| 4,427,294 A | * | 1/1984 | Nardo ........................ 356/344 |
| 4,582,990 A | * | 4/1986 | Stevens ..................... 250/328 |
| 4,676,951 A | * | 6/1987 | Armes et al. ................ 422/65 |

(List continued on next page.)

FOREIGN PATENT DOCUMENTS

| WO | WO97/32208 | 9/1997 |
| WO | WO97/35171 | 9/1997 |
| WO | WO98/15813 | 4/1998 |

(List continued on next page.)

OTHER PUBLICATIONS

D.F. Shriver et al., "The Manipulation of Air–Sensitive Compounds", Second Edition, John Wiley & Sons, Canada 1986.

D.D. Perrin et al., "Purification of Laboratory Chemicals", England 1988. Third Edition, Pergamon Press.

(List continued on next page.)

*Primary Examiner*—Jill Warden
*Assistant Examiner*—Brian Sines
(74) *Attorney, Agent, or Firm*—Ritter, Lang & Kaplan LLP

(57) ABSTRACT

An apparatus for in-situ injection of one or more chemical components into a reaction chamber is disclosed. The apparatus includes a reaction chamber for receiving one or more libraries, each of the libraries comprising two or more samples. The reaction chamber is configured to form a sealed enclosure. The apparatus further includes an injection manifold supporting injectors for in-situ injection of one or more chemical components onto respective samples of the one or more libraries in the pressurized sealed reaction chamber.

36 Claims, 12 Drawing Sheets

U.S. PATENT DOCUMENTS

| | | | | |
|---|---|---|---|---|
| 5,366,896 | A | * 11/1994 | Margrey et al. | 436/48 |
| 5,376,335 | A | 12/1994 | Gleaves | 422/80 |
| 5,593,642 | A | 1/1997 | DeWitt et al. | 422/131 |
| 5,776,359 | A | 7/1998 | Schultz et al. | 252/62.51 |
| 5,959,297 | A | 9/1999 | Weinberg et al. | 250/288 |
| 5,985,356 | A | 11/1999 | Schultz et al. | 427/8 |
| 6,004,617 | A | 12/1999 | Schultz et al. | 427/8 |
| 6,013,199 | A | 1/2000 | McFarland et al. | 252/301.4 |
| 6,030,917 | A | 2/2000 | Weinberg et al. | 502/104 |
| 6,034,240 | A | 3/2000 | McFarland et al. | 356/364 |
| 6,034,775 | A | 3/2000 | LaPointe et al. | 546/24 |
| 6,036,923 | A | * 3/2000 | Laugharn et al. | 422/82.13 |
| 6,043,363 | A | 3/2000 | LaPointe et al. | 544/225 |
| 6,045,671 | A | 4/2000 | Wu et al. | 204/298.11 |
| 6,063,633 | A | 5/2000 | Willson, III | 436/37 |
| 6,087,181 | A | 7/2000 | Cong | 436/37 |
| 6,124,476 | A | 9/2000 | Guram et al. | 549/200 |
| 6,149,882 | A | 11/2000 | Guan et al. | 422/211 |
| 6,151,123 | A | 11/2000 | Nielsen | 356/445 |
| 6,157,409 | A | 12/2000 | Riches | 356/337 |
| 6,157,449 | A | 12/2000 | Hajduk | 356/367 |
| 6,177,528 | B1 | 1/2001 | LaPointe et al. | 526/139 |
| 6,182,499 | B1 | 2/2001 | McFarland et al. | 72/24.06 |
| 6,187,164 | B1 | 2/2001 | Warren et al. | 205/81 |
| 6,203,726 | B1 | 3/2001 | Danielson et al. | 252/301.4 |
| 6,242,623 | B1 | 6/2001 | Boussie et al. | 556/18 |
| 6,248,540 | B1 | 6/2001 | Weinberg et al. | 435/7.1 |
| 6,255,487 | B1 | 7/2001 | Duchene et al. | 544/396 |
| 6,255,550 | B1 | 7/2001 | Huffman | 585/638 |
| 6,260,407 | B1 | 7/2001 | Petro et al. | 73/61.52 |
| 6,265,226 | B1 | 7/2001 | Petro et al. | 436/180 |
| 6,265,601 | B1 | 7/2001 | Guram et al. | 558/411 |
| 6,268,513 | B1 | 7/2001 | Guram et al. | 549/200 |
| 6,294,388 | B1 | 9/2001 | Petro | 436/8 |
| 6,296,771 | B1 | 10/2001 | Miroslav | 210/656 |
| 6,306,658 | B1 | * 10/2001 | Turner et al. | 436/37 |

FOREIGN PATENT DOCUMENTS

| | | |
|---|---|---|
| WO | WO00/09255 | 2/2000 |
| WO | WO 00/29844 | 5/2000 |
| WO | WO00/32308 | 6/2000 |
| WO | WO00/40331 | 7/2000 |
| WO | WO 01/21560 | 3/2001 |
| WO | WO01/93998 | 12/2001 |

OTHER PUBLICATIONS

Pangborn et al., "Safe and Convenient Procedure for Solvent Purification," American Chemical Society 1996 pp. 1518–1520, vol. 15.

Carmona, Ernesto et al., Synthesis and Properties of Dialkyl Complexes of Nickel (II). The Crystal Structure of Bis(pyridine)bis(trimethylsilylmethyl)nickel(II), J.C.S. Dalton, pp. 777–782.

Johnson, Lynda K., "New Pd(II) and Ni(II)–Based Catalysts for Polymerization of Ethylene and α–Olefins", American Chemical Society, pp. 6414–6415.

Pangborn et al., "Safe and Convenient Procedure for Solvent Purification", Organometallics 1996, pp. 1518–1520.

Copending U.S. Appl. Ser. No. 09/516,669, filed Mar. 1, 2000.

Copending U.S. Appl. No. Ser. No. 09/633,255, filed Aug. 7, 2000.

* cited by examiner

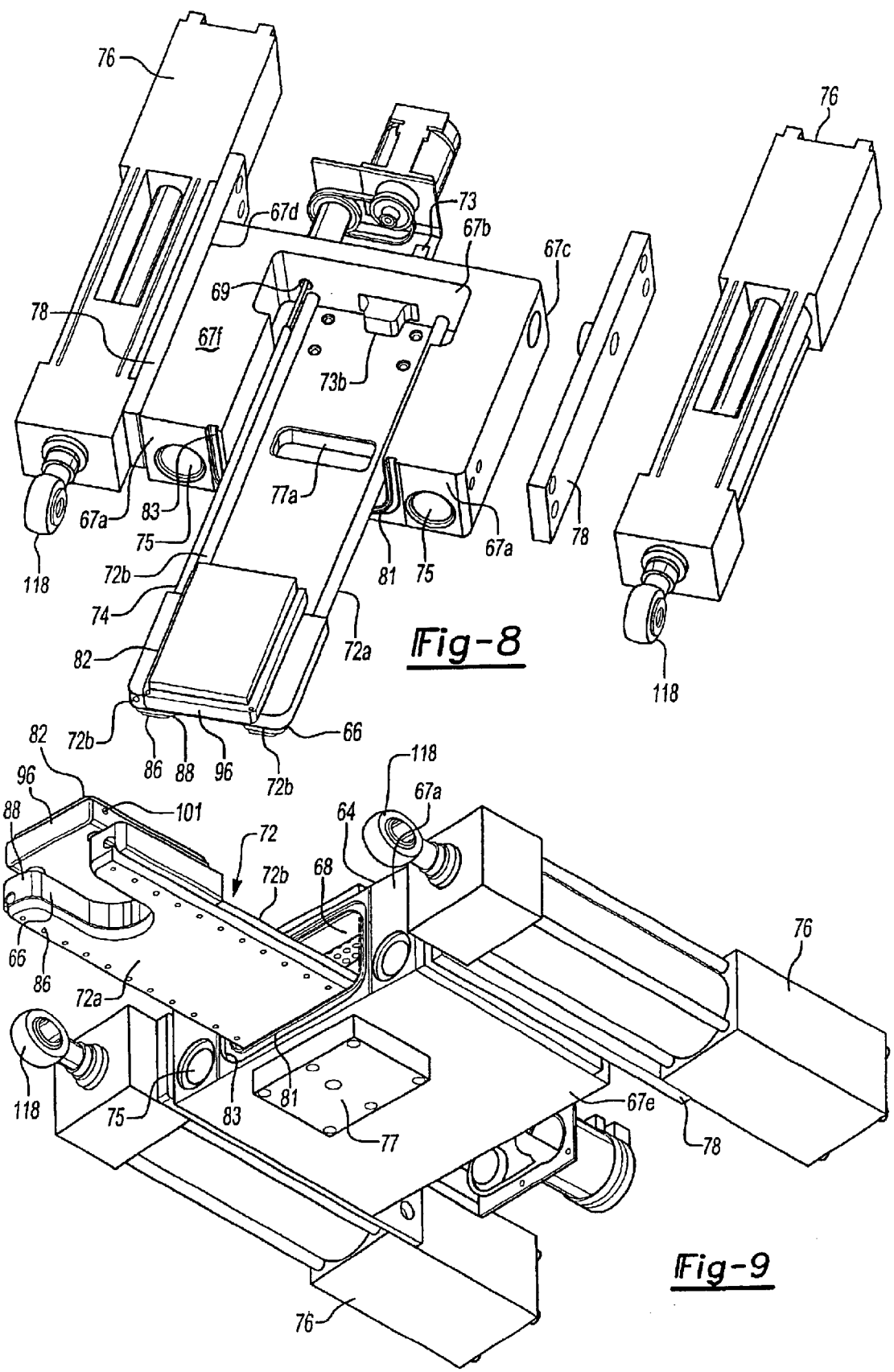

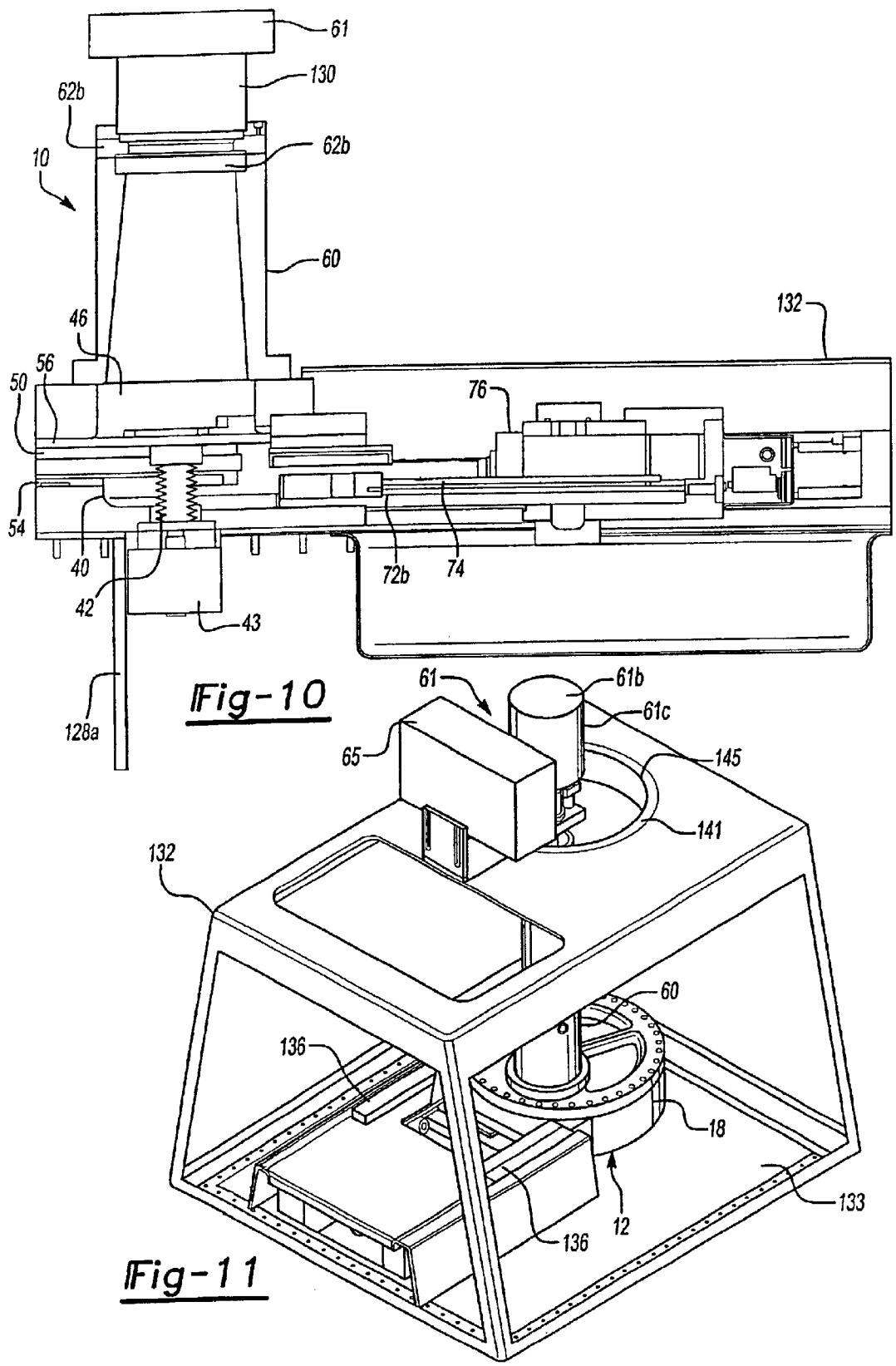

IN-SITU INJECTION AND MATERIALS SCREENING DEVICE

RELATED APPLICATION

The present application is a continuation-in-part of U.S. patent application Ser. No. 09/895,945, filed Jun. 29, 2001.

FIELD OF THE INVENTION

The present invention relates to an apparatus and method for screening two or more samples under controlled environmental conditions. More particularly, the present invention relates to an apparatus and method for permitting the screening of two or more material samples under controlled temperature and pressure, wherein one or more chemical components may be injected in-situ into the screening apparatus at ambient conditions or under pressure at any point during the screening.

BACKGROUND OF THE INVENTION

Homogeneous catalysis plays an important role in the discovery of new materials such as polymers from the polymerization or copolymerization of olefins and often involves the use of organometallic catalysts. Typically, the active organometallic catalyst is generated by treatment of a catalyst precursor with a chemical component such as a suitable activator and/or scavenger. For olefin polymerization it is often preferable to generate the active catalyst in the presence of at least one of the olefinic monomers to be polymerized and under conditions where the concentrations and ratios of the monomers being polymerized are carefully controlled.

This is partly because some catalysts will decompose more readily in the absence of the monomer(s) to be polymerized (they are, in effect, stabilized by the presence of the monomers). It is also often important to generate active catalysts in the presence of all the monomers being polymerized and under conditions where the monomer concentrations and ratios are carefully controlled because the composition, structure or properties of the polymer being produced may be adversely affected otherwise. This may be challenging for gaseous monomers such as ethylene, propylene and isobutylene where the generation of an active catalyst is generally preferably done under pressure equilibrated conditions.

The application of combinatorial methodologies to the discovery of new materials such as polymers continues to receive considerable attention in academia and industry because it has the potential to increase greatly the rate of discovery over conventional discovery methods. U.S. Pat. No. 6,030,917, incorporated herein by reference, owned by the Assignee of the present application and entitled Combinatorial Synthesis and Analysis of Organometallic Compounds and Catalysts, issued February 2000 to Weinberg et al., discusses general combinatorial methods for preparing organometallic compounds such as catalysts. And PCT Application No. PCT/US00/00418, incorporated herein by reference, published July 2000 and owned by the Assignee of the present invention, discusses library formats for ligand arrays that may be used in the application of combinatorial methodologies.

A typical workflow that utilizes combinatorial methodologies for the discovery of new catalysts such as homogeneous catalysts that may polymerize olefinic monomers involves the screening large arrays of potential catalysts for their activity. The most active catalysts may be later screened under more carefully controlled conditions to ascertain polymer properties, composition or structure.

One such method for simultaneously determining the activity of large libraries of catalysts involves the use of infrared thermography ("IRT") where a digital infrared camera is used to image (e.g., digitally photograph) the library of catalysts in the presence of one or more polymerizable monomers. Active catalysts are easily discerned from less active or inactive ones by comparing integrated temperature changes produced over time for each catalyst. See, for example, U.S. Pat. No. 6,063,633 to Wilson, entitled "Catalyst Testing Process and Apparatus," incorporated herein by reference, discussing a method and apparatus of testing a plurality of catalyst formations to determine the comparative catalytic activity of the formations in the presence of a given reactant or reactant mixture.

In a typical experiment using IRT, an array of potential catalyst precursors in a standard 96-well microtiter plate may be treated with the desired amounts of one or more polymerizable monomers, activators, scavengers or other agents that may generate or stabilize an active catalyst, and the activity of the catalysts in the array is then monitored. For experiments that involve the use of gaseous monomers such as ethylene, propylene, or isobutylene, an array of catalyst precursors is typically first treated (if necessary) with liquid co-monomers and then pressurized in a high pressure reaction chamber for a length of time suitable to allow dissolution of the gaseous monomer(s) into the individual solutions of the catalysts precursors. The reaction chamber is then typically depressurized, to allow for and activators and/or scavengers to be added to the reaction chamber. The library is returned to the reaction chamber, and the reaction chamber repressurized with the gaseous monomer to run the reaction of interest. Catalyst activity is then monitored by IRT through an infrared ("IR") transparent window mounted to the reaction chamber so as to be situated above the library and in optical contact with an infrared camera ("IR camera").

This process has been successfully used to identify active catalysts in a single 96-element array format but may be problematic in several respects. For example, the step of pressurizing the array just prior to commencing data acquisition with gaseous monomers such as ethylene may introduce unwanted thermal signatures in the data being collected. This is because during pressurization the heat of compression of the gas causes a slight increase in the local temperature of the reaction chamber and therefore the catalyst solutions in the array. When the gas has reached a final pressure and there are no pressure-volume changes or other adjustments experienced by the system, the wells in the library begin to cool down towards ambient temperature. This cooling exotherm is then superposed over exotherms generated in the system due to catalyst activity in the wells and has to be subtracted from the data gathered in order to accurately extract the heat produced by these catalytic events. This can be particularly problematic for monitoring catalysts that are not very active or where the cooling exotherm is of the same or greater scale than that of the exotherms generated due to catalysis. The cooling exotherm may also interfere with efforts to obtain reliable data early in an experiment or for catalysts that are most active early on where the thermal noise due to the cooling exotherm is greatest.

In addition, if the reaction chamber is depressurized (e.g. to allow the library to be removed so that activators may be added), the gaseous monomers begin to outgas from the solutions in the wells of the library. As a result, the gaseous monomers are no longer present at the same concentration that they were when under pressure. For polymerization reactions involving more than one olefinic monomer, this may mean that the monomer ratios are different at the time of activation. This event creates a less than ideal situation because the monomer ratio and concentration may be critical to catalyst performance as well as polymer composition, property and structure—especially for highly active catalyst systems. Moreover, the workflow described above may not be readily adapted to allow screening of more than one library at a time. This is because the aforementioned outgassing effects would be significantly exacerbated in the time between activation of successive libraries.

Therefore, it would be desirable to generate the active catalyst in-situ, and preferably, after pressure and (subsequently) temperature equilibration have been reached without the need to depressurize the reaction chamber in order to remove and activate the catalyst precursor libraries. Additionally, it would also be desirable to increase the overall experimental throughput capacity of screening systems to permit screening of multiple samples or libraries in parallel or using serial methods.

SUMMARY OF THE INVENTION

The present invention is directed to an apparatus for screening the properties or characteristics of reaction of two or more samples, wherein one or more chemical components may be injected in-situ onto the samples. The apparatus includes a reaction chamber for receiving one or more libraries. The libraries are comprised of two or more samples, preferably on a common substrate or in containers supported on a common substrate. The apparatus also includes an injection module in fluid communication with the reaction chamber. The injection process permits the in-situ injection of one or more chemical components into the reaction chamber, including while the reaction chamber has been pressurized. The apparatus also includes a selectively movable transport assembly supported by at least a portion of the reaction chamber. The transport assembly transports one or more libraries into the injection module, including while the reaction chamber has been sealed. The apparatus also includes a data gathering device for recording data determinative of one or more material or physical properties of the respective samples, individually or collectively comprising the library. The data gathering device can also record information determinative of one or more properties of the two or more samples or one or more characteristics of reactions or interactions for each of the samples, individually or collectively, or in conjunction with other chemical components.

A method for in-situ injection of one or more chemical components into a reaction chamber includes inserting one or more libraries into the reaction chamber, sealing the reaction chamber, and pressurizing the reaction chamber. The reaction chamber is allowed to reach pressure and temperature equilibrium and one or more chemical components are injected in-situ onto respective samples of the one or more libraries in the sealed reaction chamber.

BRIEF DESCRIPTION OF THE DRAWINGS

The features and inventive aspects of the present invention will become more apparent upon reading the following detailed description, claims, and drawings, of which the following is a brief description:

FIG. 8 shows a partial exploded view of the in-situ injection module and transport assembly shown in FIG. 7*a*.

FIG. 9 shows a bottom perspective view of the in-situ injection module and transport assembly shown in FIG. 7*a*.

FIG. 10 shows an elevation section view of the apparatus shown in FIG. 1, wherein a data gathering device has been added.

FIG. 11 is a perspective view of the apparatus shown in FIG. 1, wherein the apparatus has been placed in a dry box and supports an infrared camera.

DETAILED DESCRIPTION OF THE PREFERRED EMBODIMENT

Definitions

Figure 1:
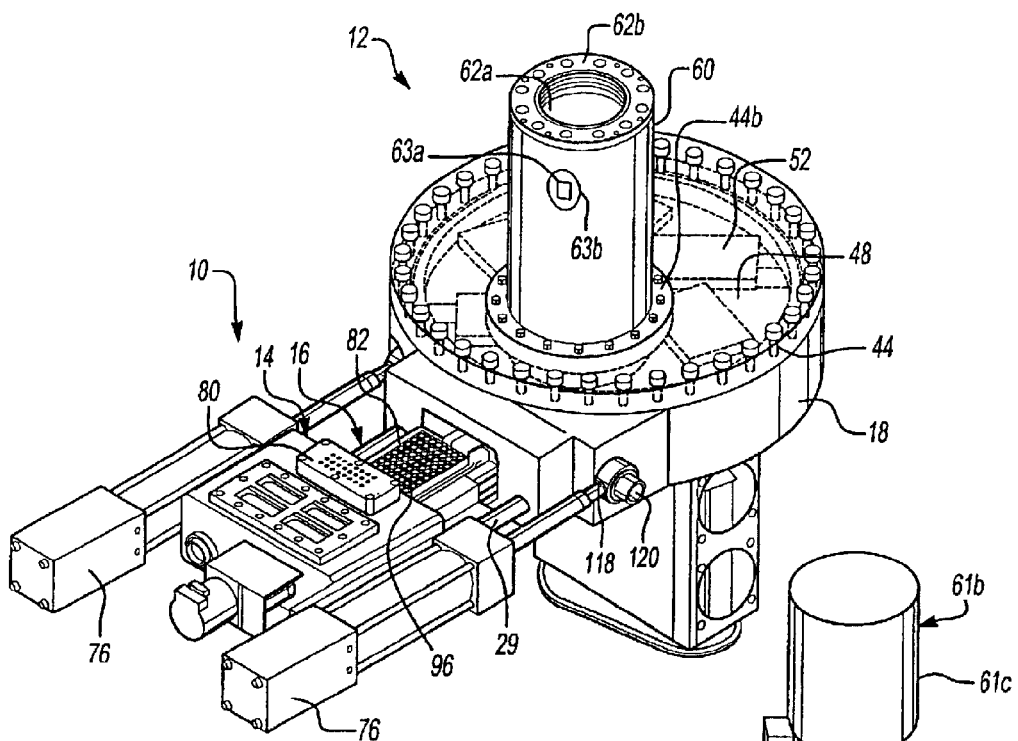
FIG. 1 is a perspective view of a material screening apparatus formed in accordance with the teachings of this invention, wherein the apparatus is shown in the open position.

The following terms are intended to have the following general meanings as used herein:

Activator: An "activator" means any chemical species that is added to a catalyst precursor that enables a catalytic process.

Charging Agent: A "charging agent" means any chemical component introduced into the reaction chamber that contacts the samples, e.g., the charging agent can be dissolved or absorbed into the sample. The charging agent may be, but is not limited to, a monomer, a catalyst, activator, scavenger or any other chemical component or agent.

Chemical Components: "Chemical components" mean any chemical species (solid, liquid or gas) that are part of an experimental design, and may include, but are not limited to, solvents, ligands, metal precursors, activators, monomers, catalysts, catalyst precursors, scavengers or other similar chemistry.

Library: A "library" means an array of samples formed on or supported by a common substrate. The library may include a plurality of different samples or may be comprised of an array of the same samples. The samples can be directly in contact with the substrate, or can be in a plurality of containers supported by a common substrate.

Scavenger: A "scavenger" means a chemical species added to remove unwanted species from the sample or reaction mixture.

Substrate: A "substrate" is a material having a rigid or semi-rigid surface. In many embodiments at least one surface of the substrate will be substantially flat. In some embodiments the substrate will contain physical separations between regions for different materials. Suitable physical separations include, for example, dimples, wells, raised regions and etched trenches. According to other embodiments, small beads or pellets may be provided on the surface, either alone or within substrate surface dimples. The surface area of the substrate is designed to meet the requirements of a particular application.

Discussion

General Description of the Apparatus

The apparatus of the present invention may be used to screen two or more samples individually or as part of a library. The screening performed by the apparatus may include the gathering of data determinative of one or more properties of the samples or one or more characteristics of reactions or interactions for each of the samples, individually or collectively, or in conjunction with other chemical components. In particular, the apparatus may be used to screen for properties such as, but not limited to, material properties such as but not limited to, melting point, glass transition temperature, thermodynamic or kinetic parameters, emissivity or physical properties such as, but not limited to, spectral properties and or Theological properties. The apparatus may also be used to screen for characteristics of reactions such as, but not limited to, conversion, selectivity, heat of reaction, kinetic profile of heat of reaction, and exothermic/endothermic profiles or other thermal events or characteristic of the respective samples. The apparatus may be operated in serial or parallel modes to perform the screening process.

In general, an apparatus for screening the samples may include an enclosed, pressure and temperature sealed reaction chamber, a transport assembly for transferring one or more libraries into the sealed reaction chamber and an injection module for permitting the injection of chemical components into the sealed reaction chamber. The injection step may occur when the sealed reaction chamber is at a temperature and pressure different from or equal to ambient conditions.

One method of using the screening apparatus includes the steps of transferring one or more libraries into the reaction chamber and sealing the reaction chamber once the libraries are in position. At this point, the chamber may be filled with a charging agent such as a monomer or other chemical components that contact the samples. For example, the charging agent may be a polymerizable olefin such as ethylene, propylene, isobutylene, etc. Once the charging agent has been added, the system may be allowed to equilibrate at a desired temperature and pressure.

While the apparatus is under equilibrated conditions, chemical components may be injected in-situ into the reaction chamber to provoke or stimulate a chemical reaction or induce other chemical or physical changes in the respective samples. The chemical components may be injected into the reaction chamber via the injection module such that the chemical components may be applied to the respective samples of a library as desired or simply injected into the reaction chamber and allowed to come into contact with the samples. More specifically, each sample plate containing a library of samples may be transported to an injection module. It will be appreciated that the apparatus may include two or more sample plates, each sample plate supporting a library of samples. More particularly, the apparatus may include four or more sample plates, and even more particularly, the apparatus may include eight or more sample plates. And even more particularly, the apparatus may include ten or more sample plates.

Regardless of the number of sample plates included in the apparatus, the transportation of the sample plates and the in-situ injection of the chemical components into the reaction chamber or directly onto respective samples may take place without increasing or decreasing the pressure in the reaction chamber. It will be appreciated that all of the libraries are exposed to the same reaction conditions, (i.e., reaction chamber temperature and pressure).

Alternatively, the apparatus may be used in, but not limited to, the following manner: the chemical components may be injected into the reaction chamber or directly onto respective samples without charging the reaction chamber, i.e., the reaction chamber is not pre-pressurized with a charging agent, or the apparatus can simply be charged with the charging agent and no other chemical components injected into the reaction chamber or onto the respective samples.

The chemical or physical changes of the samples in response to either the charging agent, or other chemical components or both may be monitored by coupling the reaction chamber to a data gathering device such as, but not limited to, an infrared camera, thermocouple, thermister or other similar device. For instance, an infrared camera may be used to monitor endothermic/exothermic reactions or other changes taking place within the library or specific samples comprising the library. Once the data gathering phase has been completed, the apparatus may be evacuated under vacuum pressure or purged with a fluid such as an inert gas and prepared for additional screenings.

Detailed Discussion of the Apparatus

A detailed description of the present invention is described herein with reference to the accompanying figures. Terms of reference such as "top," "bottom," "front," "back," or "side" are used to facilitate an understanding of the present invention in view of the accompanying figures. The identified reference terms or other similar terms are not intended to be limiting, and one of ordinary skill in the art will recognize that the present invention may be practiced in a variety of spatial orientations without departing from the spirit and scope of the invention.

FIG. 1 shows an apparatus 10 for screening two or more material samples formed in accordance with the teachings of this invention. The discussion of the apparatus 10 will consist of a discussion of the major components of the apparatus 10 followed by a discussion of how to assemble and operate the apparatus 10. The apparatus 10 includes four major components: a housing 12 defining a reaction chamber 48, an injection module 14 and a transport assembly 16.

Housing 12

Figure 3A:
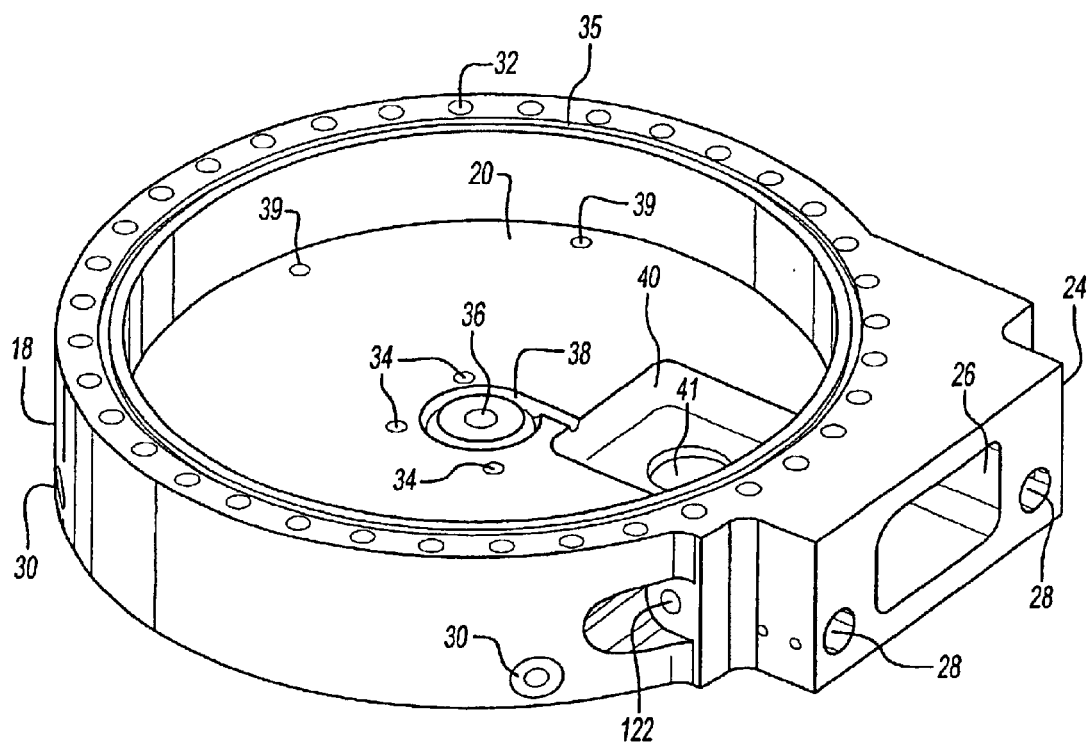
FIG. 3*a* is a perspective view showing a portion of a housing of the screening apparatus shown in FIG. 1.
Figure 4:
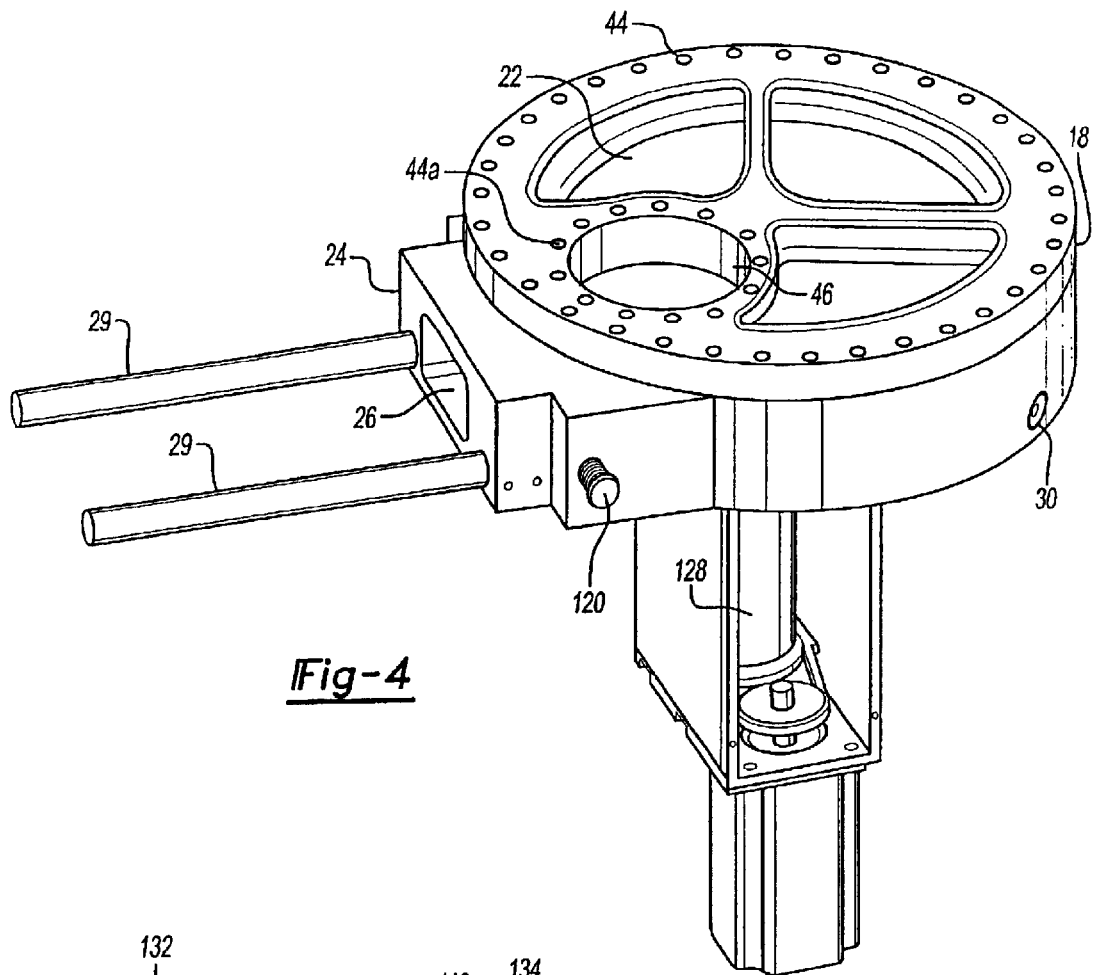
FIG. 4 shows a perspective view of the housing shown in FIG. 3*a*, wherein a cover portion has been added to the housing.

As shown in FIGS. 3a and 4, the housing 12 may include a sidewall 18, a cover 22 and a closed bottom surface 20. As best seen in FIG. 3a, the sidewall 18 may include an upstanding wall having a substantially circular configuration surrounding an open center and having an open top. It will be appreciated that the sidewall can be configured using other simple or complex geometric shapes. The thickness of the sidewall structure may vary depending on the ambient conditions and the internal pressures to which the apparatus 10 will be exposed.

As shown in FIG. 3a, the sidewall surface 18 may include a front portion that defines an outwardly extending projection 24, wherein projection 24 defines a central opening 26. The projection 24 also defines a pair of openings 28, each opening 28 being located on opposite adjacent sides of the opening 26, as illustrated in FIG. 4. The sidewall surface 18 further includes various mounting holes 32 positioned in various locations throughout the sidewall surface 18 to allow other components to be coupled to the sidewall 18 (discussed in detail below).

As seen in FIG. 3a, the sidewall surface 18 may also include an upper edge portion defining a plurality of openings 32 for receiving mechanical fasteners such as bolts or other similar devices. Also shown in FIG. 3a, the upper edge portion may also define a recessed surface area 35 adjacent the openings 32 for receiving a seal such as an O-ring seal or a gasket.

As shown in FIG. 3a, the sidewall surface 18 also includes a plurality of inlet ports 30 positioned in various locations throughout the sidewall surface 18. Each inlet 30 may be separately coupled to the same or different charging agents.

Figure 3B:
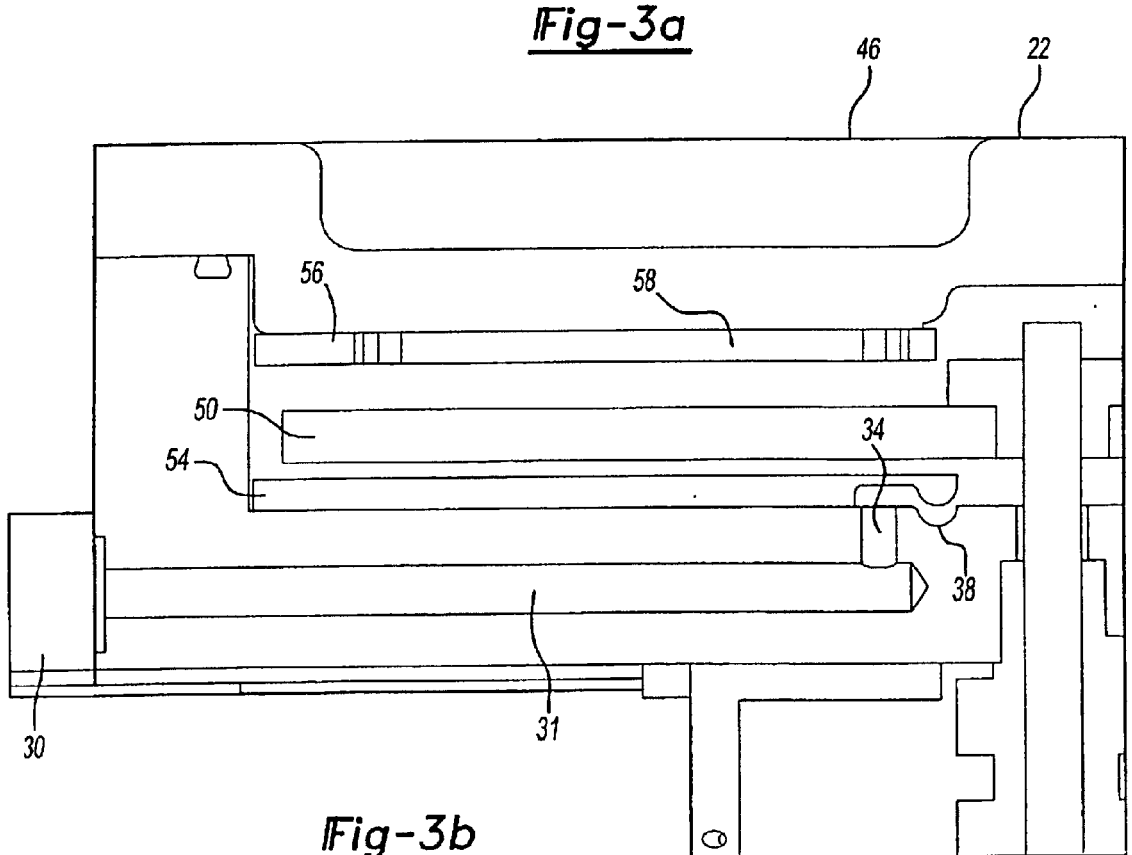
FIG. 3*b* shows a section view of the housing shown in FIG. 3*a*.

As best seen in FIG. 3b, the inlet ports 30 may include a long narrow passageway 31 through which the charging agent travels. It will be appreciated that the length of the passageway 31 can be designed to permit time for the incoming fluid to undergo temperature and pressure equilibration with the receiving environment. The exact length of the passageway 31 may be determined based on the specific fluid to be introduced into the reaction chamber. As best seen in FIGS. 3a and 3b, the inlet port passageway 31 may begin in the sidewall and continue through the bottom surface 20, terminating inside the housing 18 at exhaust ports 34 (discussed below).

As best seen in FIG. 3a, a plurality of exhaust ports 34 may be formed in the bottom surface 20. Each exhaust port 34 is in fluid communication with the inlet ports 30 previously discussed. As best seen in FIG. 3a, the exhaust ports 34 may be placed in close proximity to one another in the bottom surface 20 to help promote even dispersion of the charging agent into the reaction chamber.

Referring back to FIG. 3b, the exhaust ports 34 may include a baffle or obstruction 38 in the exhaust opening. Baffling or obstructing the exhaust opening of the exhaust ports 34 may affect a change in the direction of flow of the fluid discharged from the exhaust ports 34. In one embodiment, the baffle or obstruction 38 may be designed so as to establish a length to diameter ratio between the exhaust ports 34 and the passageway 31 to aid the charging agent's ability to reach temperature equilibrium with the receiving environment prior to dispersion therein.

As shown in FIG. 3a, the bottom surface 20 may also include an opening 36 for receiving a magnetic feed through coupled to a stepper motor driven belt drive system. The stepper motor drive imparts rotational motion to a mating part coupled thereto (discussed below). The bottom surface 20 may also define an arcuate channel 38 surrounding the opening 36 that may serve as a liquid capture well and inlet gas diverter. The bottom surface 20 also includes a recessed surface area 40 defining an opening 41 for receiving a bellows 42. Additionally, the bottom surface 20 may include various mounting openings 39 located throughout the bottom surface 20 at selected locations. Finally, the bottom surface 20 may also include lugs (not shown) for coupling to one or more pairs of jacking screws to allow readjustment of the alignment of the housing 12 if necessary.

Turning now to FIG. 4 and a discussion of the cover 22, the cover 22 may be configured having a circular configuration having a diameter sized to close the open top of the sidewall 18. The cover 22 may include openings 44 formed around the outer periphery thereof. The openings 44 may be designed to receive mechanical fasteners such as bolts or other similar devices for coupling the cover 22 to the sidewall 18. For example, bolts may be inserted into the openings 44 which are aligned with openings 32 of the sidewall 18. The openings 32, 44 are formed in the respective parts in a manner that allows the cover 22 to be positioned around the sidewall in sixty degree increments.

The cover 22 also defines an opening 46 having openings 44a formed around the outer periphery thereof. The openings 44a may be designed to receive threaded fasteners for permitting mating components to be attached to the cover 22 at the opening 46. As best seen in FIG. 3b, the opening 46 defines a viewing window into the interior of the housing 12 that permits monitoring of the samples once the housing 12 has been completely assembled. More specifically, the opening 46 or viewing window provides optical communication between the samples and a data gathering device, and more specifically a data gathering device such as, but not limited to, an IR camera.

As best seen in FIG. 1, a tube 60 may be placed over the opening 46 and may be bolted to the outer periphery of the opening 46, wherein the bolts are received in the openings 44b of the tube 60 and 44a of the cover 22. The tube 60 may include an open bottom surface and an open top surface, wherein the open bottom aligns with the opening 46, i.e., the viewing window. The top surface of the tube 60 may be closed by a transparent material coupled thereto using mechanical fasteners or other similar devices. In the disclosed embodiment, the transparent material may be any transmissive material or substance. Preferably, the transparent material is fabricated of a substance that allows electromagnetic radiation, such as, but not limited to, infrared radiation, to pass to the data gathering device. In the disclosed embodiment, the transparent material is a sapphire window 62a.

The sapphire window 62a may be coupled to the tube 60 using generally known installation and shielding techniques. For instance, as shown in FIG. 1, the sapphire window 62a may be secured to the tube 60 by a retainer 62b bolted onto the top surface of the tube 60. One of skill in the art will appreciate that other materials may be used in place of the sapphire window 62a depending upon the particular application of the apparatus 10. One of skill in the art will further appreciate that the tube 60 could be eliminated and the sapphire window 62a coupled directly to the outer periphery of the opening 46.

Figure 19:
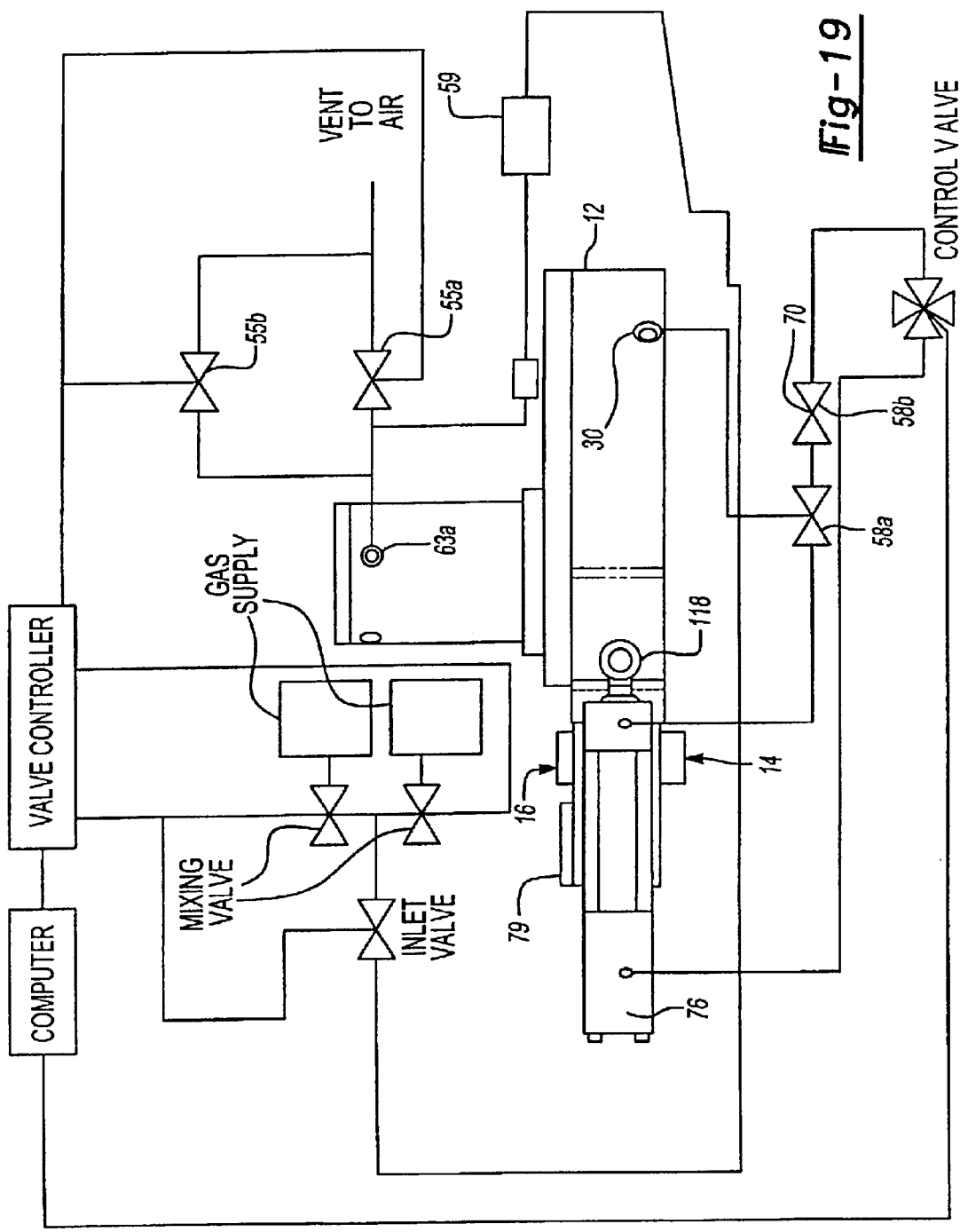
FIG. 19 shows a schematic diagram of a pressure control system that may be used in conjunction with an apparatus formed in accordance with the teachings of this invention.

Referring back to FIG. 1, the tube 60 also includes exhaust ports 63a through which the reaction chamber 48 may be vented upon the occurrence of predetermined conditions. As best illustrated in FIG. 1, the exhaust ports 63a may support gauges 63b for monitoring the internal pressure of the tube 60, and hence the pressure of the reaction chamber 48. As best illustrated in FIG. 19, exhaust ports 63a may be coupled to vent control valve 55a and a pressure release mechanism 55b.

The vent control valve 55a causes the venting of the reaction chamber upon occurrence of a predetermined pressure, and the pressure release mechanism 55b may be electrically coupled to a computer or processor that commands opening of the control valve 55a. For example, the computer can be programmed with a preset time period for performance of the screening. At the end of the preset time period, the computer issues a command causing the pressure release mechanism 55b to open, releasing the pressure in the reaction chamber. It will be understood that the vent control valve 55a could be controlled manually rather than computer controlled.

Additionally, the interior surface of the tube 60 may support various sensors such as pressure and temperature transducers or other similar devices (not shown) for measuring the internal pressure and temperature of the tube 60. One of skill in the art will appreciate that all gauges or sensors coupled to the tube 60 could be monitored manually or via computer.

The housing 12, as defined by the sidewall 18, cover 22, bottom surface 20 and tube 60, may be formed of a metal or composite material. Preferably, the material chosen for fabricating the housing 12 will have a high thermal conductivity. In the disclosed embodiment, the housing 12 may be fabricated using aluminum, and more particularly, 6000 series aluminum. The housing 12 may also be black anodized Teflon® sealed. It will be appreciated that Teflon® is a trademark of E.I. duPont de Nemours & Co. (hereinafter "DuPont") located at Wilmington, Del., 19898, (302) 999-4592. One of skill in the art will understand that Teflon® is a trademark identifying a compound comprising polytetraflouro ethylene. And one of skill in the art would also understand that other materials having similar properties could be used including, but not limited to, other fluoropolymer resins. One of skill in the art will further understand that other materials having sufficient thermal, material or corrosion resistant properties may be used to fabricate the housing 12.

The fully assembled and sealed housing 12, i.e., the opening 26 in the sidewall surface 18 has been closed and sealed, may be pressurized and maintained in pressure and temperature equilibrated conditions for a predetermined time period. The housing 12 can be designed to withstand predetermined pressure and stress levels. Finite element analysis can be used to calculate the anticipated stress levels, and one of skill in the art will appreciate that the exact dimensions of the housing 12 will vary depending on the stress and pressure levels to which the housing 12 will be exposed. In the disclosed embodiment, the housing 12 is designed to withstand an internal maximum pressure of approximately 200 PSI, vacuum pressure levels of approximately $10^{-4}$ Torr, and to withstand, at a minimum, stresses of approximately 3.0 times the yield strength and 1.5 times the tensile strength of the material forming the housing. The housing 12 may also be designed, for example, to operate at pressures of 5 PSI, 10 PSI, 50 PSI, 100, PSI, 500 PSI, 1000 PSI, or other selected pressures.

Reaction Chamber 48

Figure 5A:
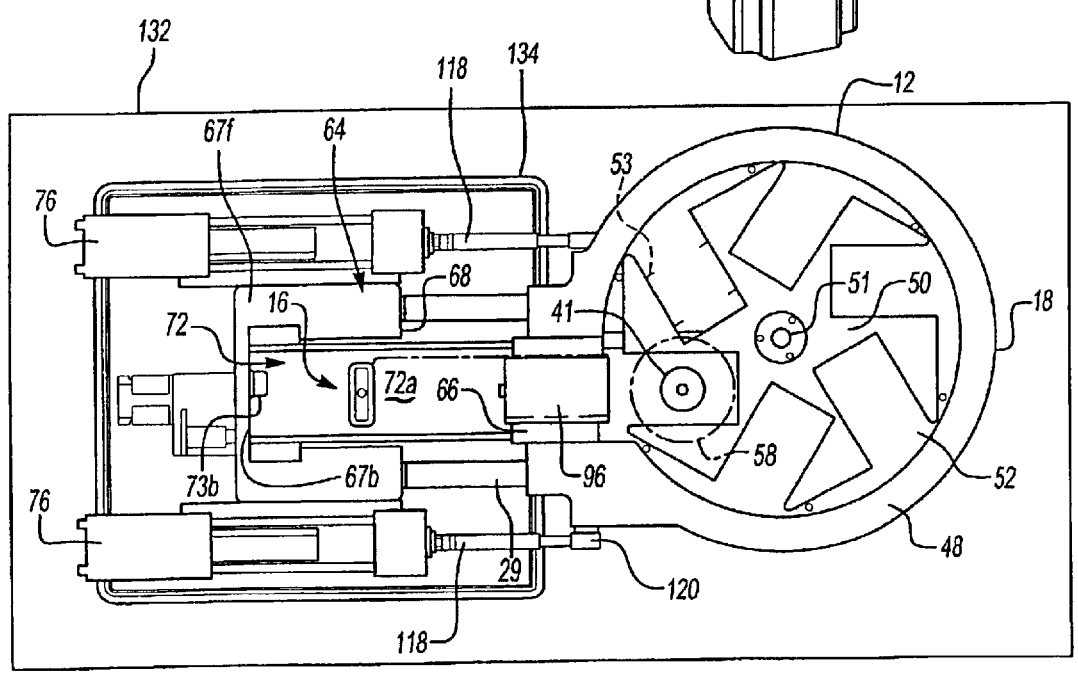
FIG. 5*a* shows a top section view of the screening apparatus shown in FIG. 1.

Referring now to FIG. 5a, the housing 12 defines the second major component of the apparatus 10, the reaction chamber 48. The reaction chamber 48 is defined by the inwardly facing surfaces of the partially open sidewall 18, bottom surface 20 and cover 22. Thus, the reaction chamber 48 as defined by the housing 12 comprises the open center defined by the surfaces 18, 20 and 22, and is partially open to ambient conditions due to the opening 26 formed through sidewall surface 18. As will be discussed in more detail below, the reaction chamber 48 may be closed by sealing the opening 26.

As best seen in FIGS. 3b and 5a, the reaction chamber 48 may retain a carousel 50, a first spacer plate 54 and a second spacer plate 56. The carousel 50 may be designed to accommodate one or more libraries for screening. The carousel 50 may be configured as a circular plate; however, other geometric configurations such as, but not limited to quadrilaterals, hexagons, octagons or triangles may be used.

Figure 5B:
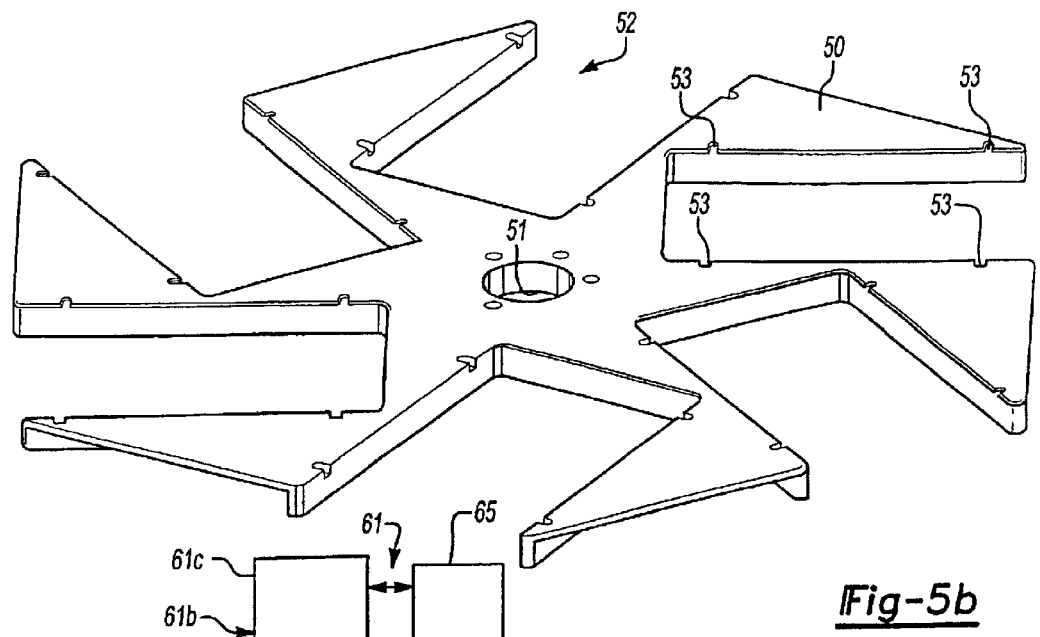
FIG. 5*b* is a perspective view of a carousel for use in the present invention formed in accordance with the teachings of this invention.

The carousel 50 may include one or more open top and bottom slots 52 for receiving a library of samples. Each slot 52 may include an opening that may be rectangular in shape. However, one of skill in the art will appreciate that the opening may be configured of various geometric shapes, including but not limited to, a circle, square, triangle, diamond, octagon or other complex or simple geometric designs. The outer periphery of each slot 52 may define a pair of indents 53, shown in FIG. 5b by the phantom lines. In the disclosed embodiment, the indents 53 are formed adjacent the corners of opposing sidewalls along the outer periphery of the length of the slot 52. The carousel 50 may also include a central opening 51 for coupling the carousel 50 to a stepper motor driven magnetic feed through for driving the carousel 50.

The carousel 50 may be fabricated of a metal, plastic or composite material. In the disclosed embodiment, the carousel 50 may be fabricated of aluminum, more particularly 7075 grade aluminum. However, one of skill in the art will appreciate that other materials having similar chemical, thermal and material properties could be used to fabricate the carousel 50.

The carousel 50 may be rotatably received in the reaction chamber 48 by coupling the carousel 50 coupled to a magnetic feed through 128 using known techniques to permit selective movement of the carousel 50. The magnetic feed through 128 is of the type conventionally used in the industry.

Figure 6:
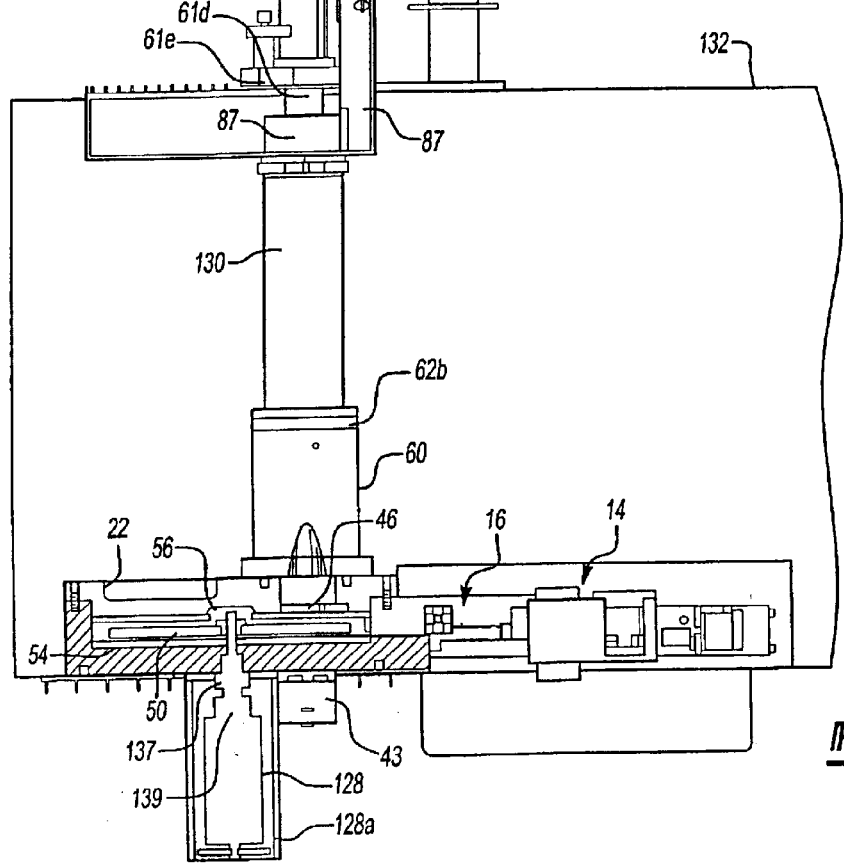
FIG. 6 shows an elevation section view of the apparatus shown in FIG. 2.

As best seen in FIG. 6, the magnetic feed through 128 is received in aligned central openings 36 and 51, formed respectively in the bottom plate 20 of the housing 12 and the carousel 50. One end of the magnetic feed through 128 may be coupled to a stepper motor driven belt drive system using known techniques, and the opposite end of the magnetic feed through may be coupled to the carousel 50 also using generally known techniques. As best seen in FIG. 4, the magnetic feed through 128 may be placed inside a sealed housing, wherein a portion of the housing is coupled to the housing 12. One of skill in the art will appreciate that other drive systems, including conventional gear drive systems, could be used to drive the rotation of the carousel 50.

As best seen in FIG. 6, the carousel 50 may be positioned in the reaction chamber 48 between first and second spacer plates 54, 56. The first and second spacer plates 54, 56 may be circular plates. One of skill in the art will appreciate that other simple or complex geometric shapes could be used. Also, as shown in FIG. 3b, the second spacer plate 56 may include an opening 58, which opening 58 may provide an opening for viewing or observing the slots 52 defined by the carrousel 50.

The spacer plates 54, 56 can be fabricated of a metal, plastic or composite material. In the disclosed embodiment, the first and second spacer plates 54, 56 are constructed using a material having a high thermal conductivity, the preferred material being aluminum, specifically 6061-T6 grade aluminum. However, one of skill in the art will appreciate that other materials having suitable heat transfer properties may be used.

The first and second spacer plates 54, 56 may be adjustably positioned within the reaction chamber 48 to permit the volume of space above and below the carousel 50 to be varied. The spacer plates 54, 56 may also be configured to permit the volume of space surrounding the carousel 50 to be adjusted. For example, the first spacer plate 54 may be mounted below the carousel 50, and may be attached to the bottom surface 20 by mechanical fasteners such as screws received in the opening 39 and mating openings formed in the first spacer plate 54. In the disclosed embodiment, the distance of the first plate 54 below the carousel 50 may be adjusted to permit adjustment of the volume of the reaction chamber 48 below the spacer plate 54.

As shown in FIG. 6, the second spacer plate 56 may also be adjustably coupled to the interior of the sidewall 18 using mechanical fasteners such as screws, and thus may permit customization of the volume of the reaction chamber 48 above the carrousel 50. This arrangement permits accommodation of variously sized components in the upper portion of the reaction chamber 48.

The first spacer plate 54 may also act as a baffle to help disperse at least a portion of the chemical charging agent introduced into the bottom of the reaction chamber 48 through the exhaust ports 34 defined by the bottom surface 20.

In an alternative embodiment, the reaction chamber 48 may be designed such that the spacer plates 54, 56 may be omitted, i.e., the volume of the reaction chamber 48 is defined such that the spacer plates 54, 56 are not need for volume adjustment.

In-situ Injection Module 14

Figure 7A:
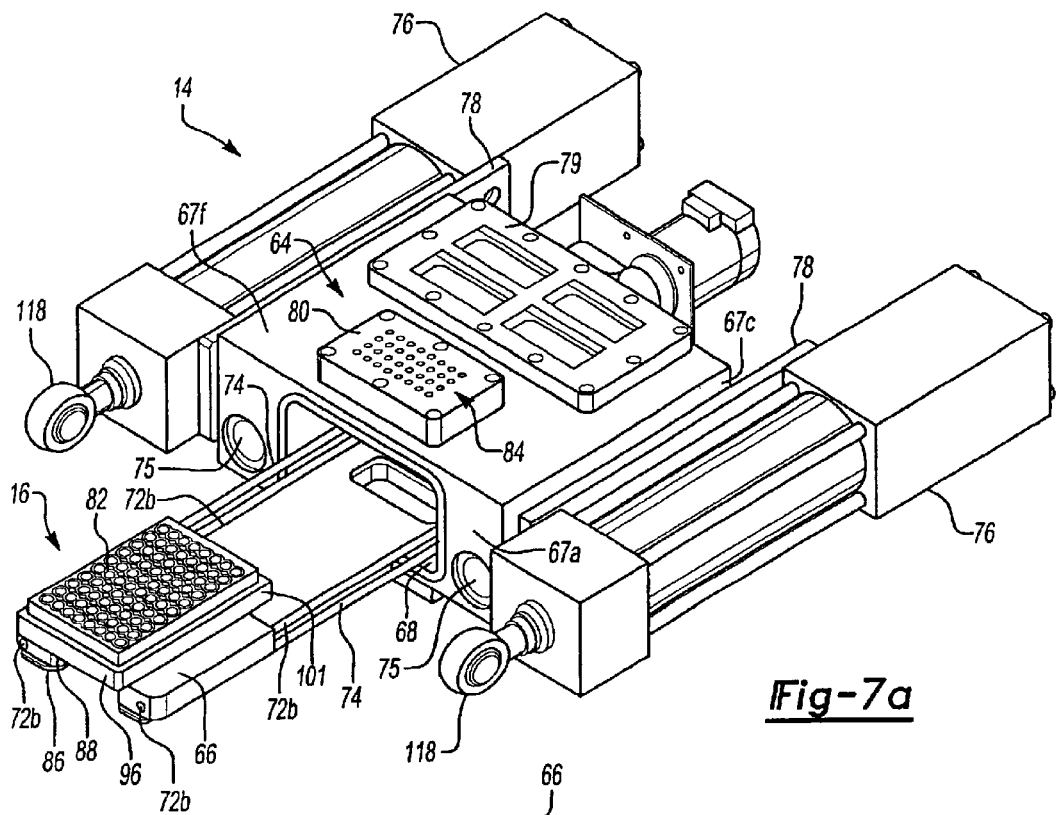
FIG. 7*a* shows a perspective view of an in-situ injection module and a transport assembly formed in accordance with the teachings of this invention.

Turning now to FIG. 7a and a discussion of the third major component of the apparatus 10, the in-situ injection module 14, the in-situ injection module 14 allows one or more chemical components to be injected or introduced in-situ into the reaction chamber 48. The reaction chamber 48 may be at a pressure the same as or different from ambient conditions during the injection. And if the reaction chamber 48 is at a pressure different from ambient pressure, the injection can take place without increasing or decreasing the pressure in the reaction chamber 48.

The in-situ injection module 14 may be used in a variety of applications where it may be desirable to introduce chemical components into a vessel, where the vessel can be maintained at ambient or other pressure conditions. In its most general form, the in-situ injection module 14 may include an injection manifold supported by the vessel into which a fluid may be to be injected. The injection manifold may include a plurality of openings, each opening and the interface of the injection manifold with the vessel being sealed to isolate the vessel from ambient conditions. And the injection manifold may be coupled to one or more injectors that are attached to one or more sources of chemical components. In an alternative embodiment, the injection manifold is supported by reaction chamber housing 12.

As best seen in FIG. 7a, the in-situ injection module 14 may include a selectively movable housing 64 that supports an injection manifold 80. The housing 64 may perform two primary functions: (1) supporting the injection manifold 80 and (2) sealing the partially enclosed reaction chamber 48.

As best seen in FIGS. 7a and 8, the housing 64 may include front, rear, right/left side, bottom and top surfaces 67a–e, respectively, and may be constructed using a metal or composite material. Preferably, the material chosen will have a high thermal conductivity to permit rapid dissipation of heat through the housing 64, as the development of a substantial temperature gradient through the housing 64 may interfere with the measurements taken during the sample screening process. In the disclosed embodiment, the housing 64 may be formed of aluminum, and more particularly 6061-T6 grade aluminum. One of skill in the art will appreciate that other materials having similar chemical, material and thermal properties may be used to construct the housing 64.

As best seen in FIGS. 7a and 8, the front, rear right/left sides, bottom and top surfaces 67a–e comprising the housing 64 define a rectangular configuration. More specifically, each surface 67a–f defines a substantially planar surface area having various openings. The particular attributes and function of each surface 67a–f will be described below.

As shown in FIG. 7a, the top surface 67f defines a substantially flat surface area, and supports the injection manifold 80, hence, performance of the first primary function of the housing 64. The injection manifold 80 may be integrally formed with housing 64 or formed as a separate component. If formed as a separate component, the injection manifold 80 may be affixed to the top surface 67f using welding or other similar techniques. In the disclosed embodiment, the injection manifold 80 is coupled to the top surface 67f using mechanical fasteners such as screws. The interface between the injection manifold 80 and the top surface 67f may be sealed to isolate the internal pressure of the housing 64 from ambient conditions. For instance, an O-ring seal or other similar device can be used.

As best seen in FIG. 7a, the injection manifold 80 may include a plurality of openings 84 in fluid communication with the interior of the housing 64. One of skill in the art will appreciate, however, that the mating surfaces of the respective openings 84 and the top surface 67f may be sealed to isolate the internal pressure of the housing 64 from ambient conditions.

Figure 18:
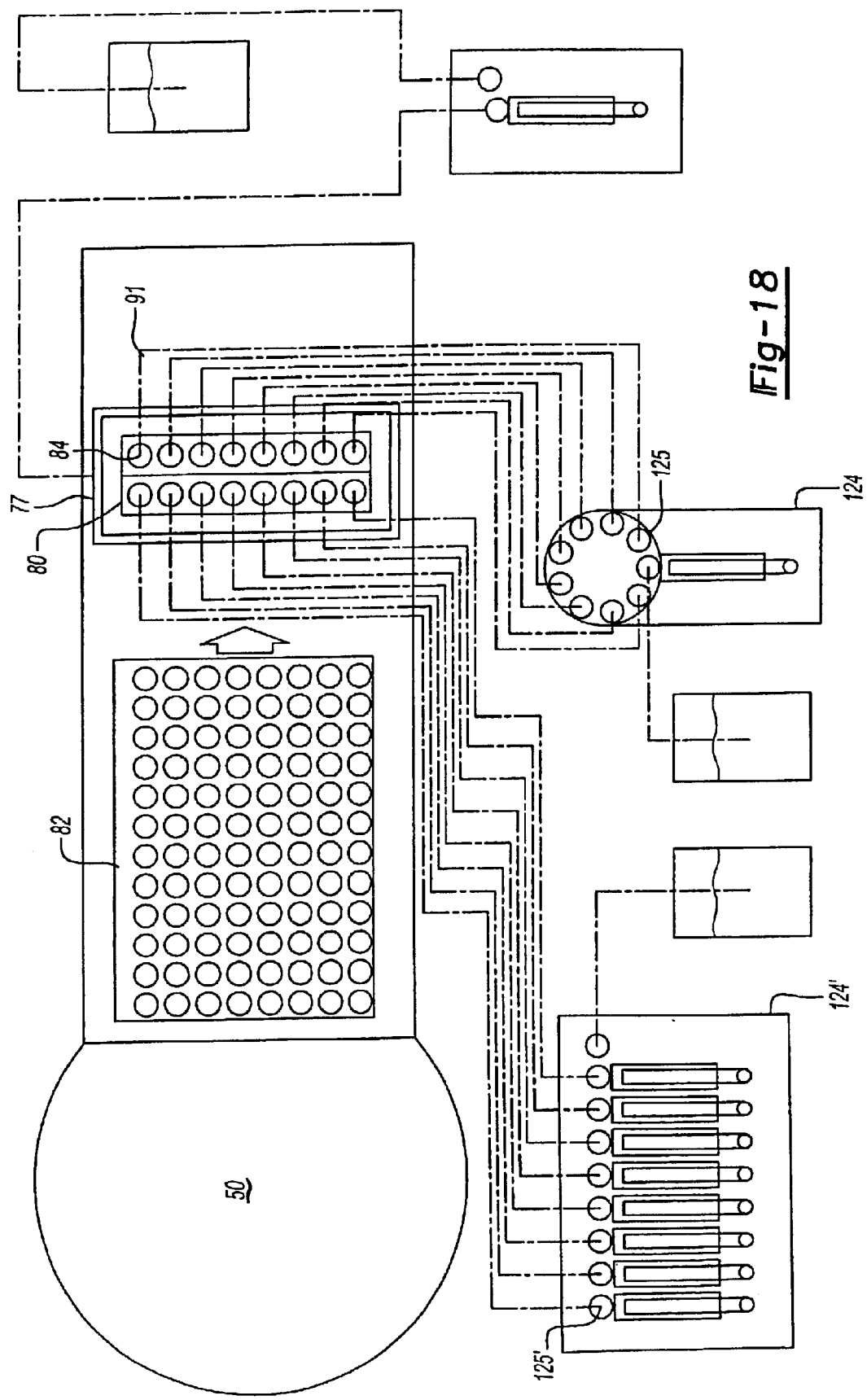
FIG. 18 shows one embodiment of an apparatus formed in accordance with the teaching of this invention coupled to a source of chemical components.

As best seen in FIG. 18, each opening 84 may be coupled to one or more injectors that may be separately coupled to a supply of chemical components. For example, as shown in FIG. 18, the openings 84 of the injection manifold 80 are coupled to respective injectors. Each of the injectors may be coupled to separate injector lines 91 in accordance with known techniques. As best seen in FIG. 18, each injector line 91 may be coupled to a single multi-channel serial pump 124 using known fastening techniques.

As best seen in FIG. 18, the pump 124 includes eight outlets or channels 125, wherein each channel 125 may be rotated serially into fluid communication with each of the injector lines 91. The pump 124 is of a type known in the industry, and one of skill in the art would understand how the pump 124 operates. Thus, a detailed description of the operation of the pump will not be discussed.

The multi-channel serial pump 124 permits each outlet 125 to be coupled to different chemical components, including solvents. Thus, each injector line 91 may receive one or more chemical components during the course of the experiment.

In an alternative embodiment, each injector 89 may be coupled to a separate pump and supply of chemical components. In still another embodiment, the pump used in the apparatus 10 can be a parallel pump 124' of the type known and used in the industry, and illustrated schematically in FIG. 18. As shown, each pump 124' is coupled to separate injectors and a common fluid supply via channels 125'.

As shown in FIG. 7a, in addition to supporting the injection manifold, the housing 64 includes sufficient surface area to allow the support of other components. For instance, the top surface 67f also supports an electrical feed through 79 for coupling electronic or electrical components to a library or individual wells of the library. One of skill in the art will appreciate that the electronic or electrical components may be used for purposes of data gathering, equipment control or for heating or cooling the libraries to a temperature different from ambient temperature. One of skill in the art will also appreciate that the passageways into the housing 64 from the electrical feed through 79 are sealed to isolate the internal pressure of housing 64 from ambient conditions.

As best seen in FIG. 8, the rear surface 67b may include an opening 69 for receiving a magnetic feed through stepper motor driven belt drive assembly. The rear surface 67b may also support a gauss level sensor 73b for homing the selectively movable carriage 66 (discussed in detail below).

Referring now to FIGS. 7a and 8, the front surface 67a defines a channel 68 that extends through the housing 64 and terminates at the rear surface 67b, as best seen in FIG. 8. The channel 68 may include a raised lip 81 bounded by a recess surface area 83 as best seen in FIG. 9.

As shown in FIG. 9, the bottom surface 67e may support a wash basin 77 that acts a liquid capture well. The wash basin 77 may be a metal block defining an open center 77a, wherein the open center 77a is in fluid communication with the interior portion of the housing 64. It will be appreciated that the fluid path between the wash basin 77 and the housing 64 may be sealed so as to isolate the internal pressure and temperature of the housing 64 from ambient pressure and temperature.

As best seen in FIG. 9, the wash basin 77 is coupled to the bottom surface using mechanical fasteners such as bolts. One of skill in the art will appreciate that other similar devices or known fastening techniques could be used.

Figure 2:
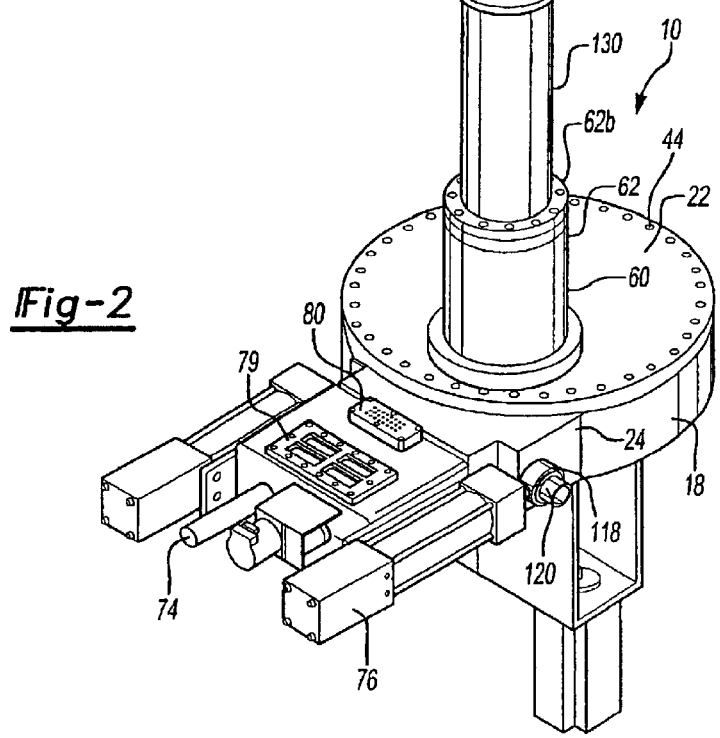
FIG. 2 is a perspective view of the screening apparatus shown in FIG. 1, wherein the apparatus includes a data gather device coupled thereto and is shown in the closed position.

As best seen in FIG. 2, to perform the second primary function of sealing the reaction chamber 48, the housing 64 may be designed to move over a linear path until the housing 64 contacts the housing 12. The movement of the housing 64 is caused by the retraction and extension of pneumatic cylinders 76.

The cylinders 76 are supported on the right/left surfaces 67c, 67d of the housing 64 by intermediate mounting plates 78, as best seen in FIGS. 7 and 8. As shown in FIG. 4, one end of the rods of the pneumatic cylinders 76 may support a fitting 118 that may be coupled to cylinder mounting bolts 120 received in a threaded opening 122 defined by the housing 12. The sealing contact between the front surface 67a and the front surface 24 of the housing 12 may be sealed by an O-ring seal.

The pneumatic cylinders 76 are lock on retract-type cylinders, which are well known in the industry. For example, once the pneumatic cylinders 76 are retracted, the pneumatic cylinders 76 become locked in the retracted position. The pneumatic cylinders 76 will remain in the locked position until the opposite side of the cylinder housing is pressurized. The locking mechanism for the pneumatic cylinders 76 is a mechanical lock as opposed to a friction lock.

The operation of the cylinders 76 may be controlled manually or via a computer, wherein the computer can issue a command causing air under pressure to flow in the cylinder chamber, causing retraction of the cylinders 76. This arrangement brings the housing 64 into sealing contact with the house 12, and the application of air pressure to the opposite side of they cylinders 76 separates the housings 12, 64.

As shown in FIG. 19, the cylinders 76 are coupled to two solenoid valves shown schematically as 58a, 58b. Both solenoid valves 58a, 58b are coupled to a relay 59, wherein the relay is essentially a pressure sensor. When the pressure of the reaction chamber 48 exceeds a set point, for example 5 PSI, the relay 59 disconnects power from the solenoid valve 58a. Thus, the solenoid valve 58a closes, disconnecting pneumatic control of the pneumatic cylinders. The other solenoid valve 58b is electrically coupled to the power supply for the apparatus 10, and when the relay 59 is activated, the solenoid 58b is disconnected from the power supply to the apparatus 10. It will be appreciated that the preset pressure for activating the relay 59 could be set higher or lower than the 5 PSI setting discussed herein. It will be appreciated that a single solenoid valve 58a may be coupled to the relay 59 rather than two as described herein.

In operation, the simultaneous extension and retraction of each rod of the pneumatic cylinders 76 causes the housing 64 to traverse a linear path. One of skill in the art will appreciate that hydraulic or electrically operated cylinders could be substituted for the pneumatic cylinders 76. One of skill in the art will also appreciate that other conventional linear drive systems such as a rack and pinion, or gear drives could be used in place of the pair of pneumatic cylinders 76. It will also be appreciated that the cylinder 76 may be operated manually.

Referring now to FIG. 11, the movement of the housing 64 toward the housing 12 may be disrupted by a pair of light gate sensors 136 located adjacent the sidewall surfaces 18, 67c, 67d, respectively, of the housings 12 and 64. As best seen in FIG. 11, the light gate sensor 136 is detached from the housings 12, 64 and positioned along the sidewall surfaces 18, 67c, 67d, respectively, of the housings 12 and 64. The pair of sensors 136 directs a light beam laterally between the sensors 136 so as to cross the path between the housings 12 and 64. If the light beam is broken, the sensors 136 may interrupt the closing motion of the housing 64. In an alternative embodiment, the pair of light gate sensors 136 could be affixed to a portion of one or both housings 12 and 64.

The light gate sensor 136 may be disabled when the housing 64 is in sealing engagement with the housing 12 and the pneumatic cylinders 76 are applying sealing pressure to the front surface of housing 12. In this instance, an override system disables the light gate sensor 136 when both cylinders 76 are retracted and locked automatically.

Transport Assembly 16

Turning now to FIGS. 8–9 and a discussion of the fourth major component of the apparatus 10, the transport assembly 16, the transport assembly 16 allows one or more components to be transported within the reaction chamber 48 using a conveyor-type assembly. The transport assembly 16 may be used in a variety of applications where it is desirable to transport items from one location to another, particularly where the items to be transported are retained in a confined pressurized area.

One function of the transport assembly 16 in the apparatus 10 is to allow one or more libraries to be transported to and from one or more locations within the reaction chamber 48 and from the reaction chamber 48 to and from the housing 12 or the housing 64. The libraries may be transported within the reaction chamber 48, the housing 12 or the housing 64 while the reaction chamber 48 is at a temperature and pressure that may be equal to or different from ambient conditions.

As best seen in FIG. 8, the transport assembly 16 may include a support assembly 72 for supporting a selectively movable carriage 66. As best seen in FIG. 5a, the support assembly 72 may include a linear slide plate 72a having an elongated rectangular surface fabricated of a high thermal conductive material. In the disclosed embodiment, the linear slide plate 72a is fabricated of 6061-T6 aluminum. However, one of skill in the art will appreciate that other materials having similar thermal and material properties could be used.

As best seen in FIG. 9, the sidewall surface of the linear slide plate 72a may include a plurality of openings for receiving fasteners for coupling linear slides 72b thereto. The elongated rectangular surface of the linear slide plate 72a may also include a distal end and a proximate end. As shown in FIG. 9, the distal end of the linear slide plate 72a may define a U-shaped portion 86 for receiving with adjacent components when the linear slide plate 72a is fully assembled. In an alternative embodiment, the linear slide plate 72a could be eliminated, leaving the linear slides 72b as the only component of the support assembly 72.

As best seen in FIG. 5a, the linear slide plate 72a adjoins the housings 12 and 64 using conventional techniques. For example, the linear slide plate 72a is mounted in the channel 68 defined by the housing 64. The proximate end of the linear slide plate 72a is coupled to the bottom surface of the housing 64 using mechanical fasteners such as screws, as best seen in FIG. 8. The distal end of the linear slide plate projects a predetermined distance beyond the front edge of the channel 68.

As shown in FIG. 8, the linear slide plate 72a extends beyond the channel 68 a distance equal to the desired distance between the rear surface 67b and the recessed surface area 40 defined by the bottom surface 20 of the housing 12. As best seen in FIG. 5a, the linear slide plate 72a extends between the rear surface 67b of the housing 64 and the recessed surface 40 of the housing 12. Inside the housing 12, the U-shaped portion 86 of the linear slide 72a rests within the recess 40 defining the opening 41 such that the open 41 is centrally located between the opposing surfaces of the U-shaped portion 86.

As shown in FIG. 10, the U-shaped portion 86 is sized to receive a bellows 42 that is received in the opening 41 formed in the recessed surface area 40. The bellows 42 may be coupled to a pneumatic cylinder 43 as shown in FIG. 10. One of skill in the art will appreciate that conventional techniques may be used to couple the bellows 42 to the pneumatic cylinder 43. One of skill in the art will further appreciate that the point of entry of the bellows 42 into the housing 12 may be sealed using an O-ring seal or other similar device.

In an alternative embodiment, the transport module 16 could be configured to permit the samples to be transferred to the injection module 14 via rotational or translational movement rather than linear movement.

Turning now to FIGS. 8 and 9 and a discussion of the carriage 66, the carriage 66 may include a rectangular configuration having a U-shaped end portion 88 that aligns with the U-shaped portion 86 of the linear slide plate 72a. The carriage 66 may be fabricated of a material having a high thermal resistivity. In the disclosed embodiment, the carriage 66 is fabricated of a polymer material, with the preferred material being Teflon® available from DuPont.

Figure 7B:
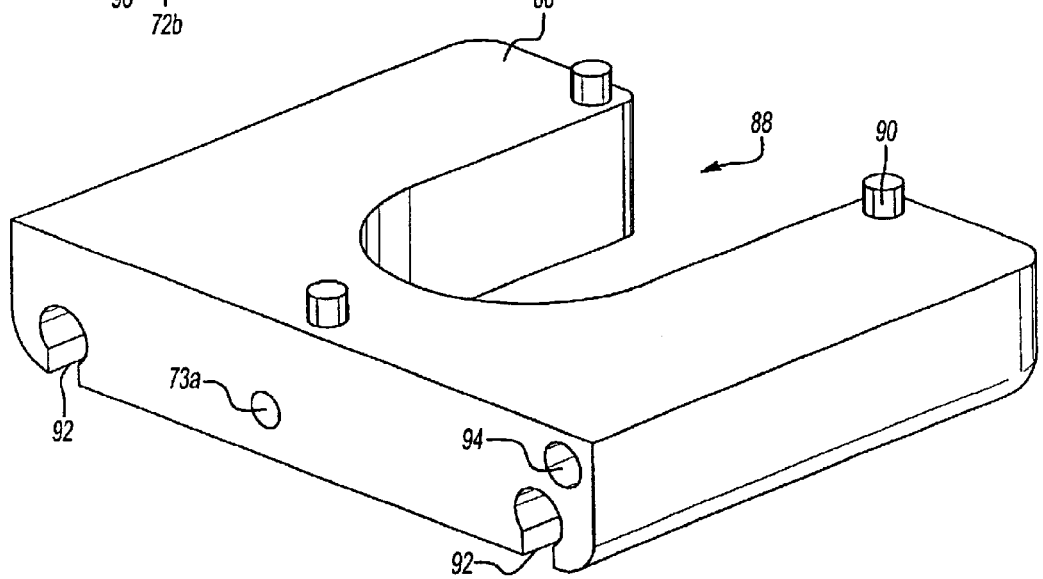
FIG. 7*b* is a detail view of a carriage forming a portion of the transport assembly shown in FIG. 7*a*.

As best seen in FIG. 7b, the top surface of the carriage 66 may support one or more outwardly projecting alignment studs 90 at the periphery of the U-shaped portion 88 and at the rear of the carriage 66. As best seen in FIG. 7b, the carriage 66 defines slots 92 that extend the length of the carriage 66. Each slot 92 receives and supports one of the linear slides 72b of the transport assembly 16.

The carriage 66 also defines a threaded opening 94 for receiving a threaded rod 74 for imparting controlled linear movement to the carriage 66. The threaded rod 74 may be an acme screw, and as best seen in FIG. 8, the threaded rod 74 may be coupled to a magnetic feed through, which, in turn, may be coupled to a stepper motor driven belt drive system. One of skill in the art will appreciate that the magnetic feed through may be enclosed in a casing as shown in FIG. 6 in order to provide a barrier or seal isolating the access points of the drive system into the housing 64 from ambient pressure and temperature.

It will be appreciated that the carriage 66 may be caused to traverse the linear slide plate 72a by sliding along the linear slides 72b upon rotation of the threaded rod 74 coupled to the carriage 66. For instance, one end of the threaded rod 74 is received in the threaded opening 94 of the carriage 66, and the other end is coupled to a magnetic feed through drive system. As the threaded rod 74 rotates in a clockwise direction, the carriage 66 slides along the linear slide plate 72a, in the direction of the housing 12. When the threaded rod 74 rotates in the counterclockwise direction, the carriage 66 slides away from the housing 12.

The carriage 66, as best seen in FIG. 7b may also support a homing magnet 73a. The homing magnet 73a cooperates with a second sensor such as a gauss level sensor 73b supported by the housing 64 to calibrate the carriage 66 to a preset home or start position. The homing magnet 73a and the gauss level sensor 73b cooperate to control the distance that the carriage 66 will travel when the transport assembly 16 is activated. For instance, the carriage 66 home or starting position established due to the cooperation of the homing magnet 73a and the gauss level sensor 73b is programmed into a computer. The computer monitors and controls the movement of the carriage 66 using the home or starting position as a reference.

Figure 13:
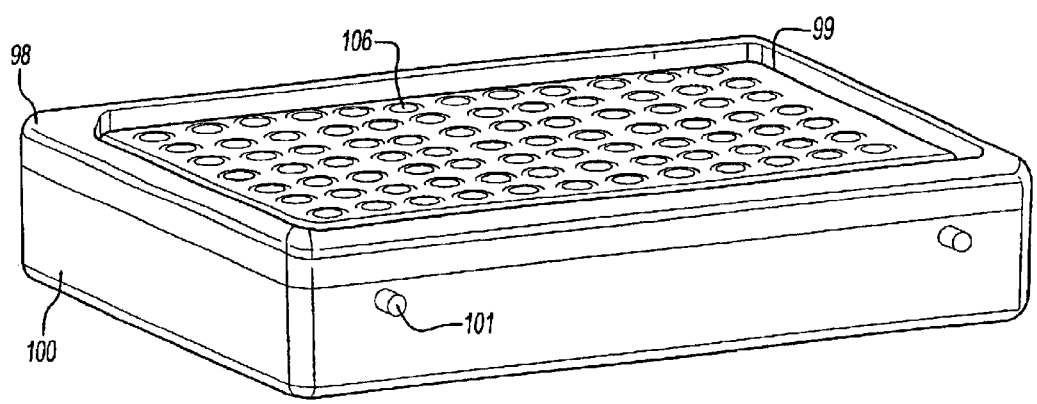
FIG. 13 is a perspective view of a sled or sample support plate formed in accordance with the teachings of this invention.
Figure 14:
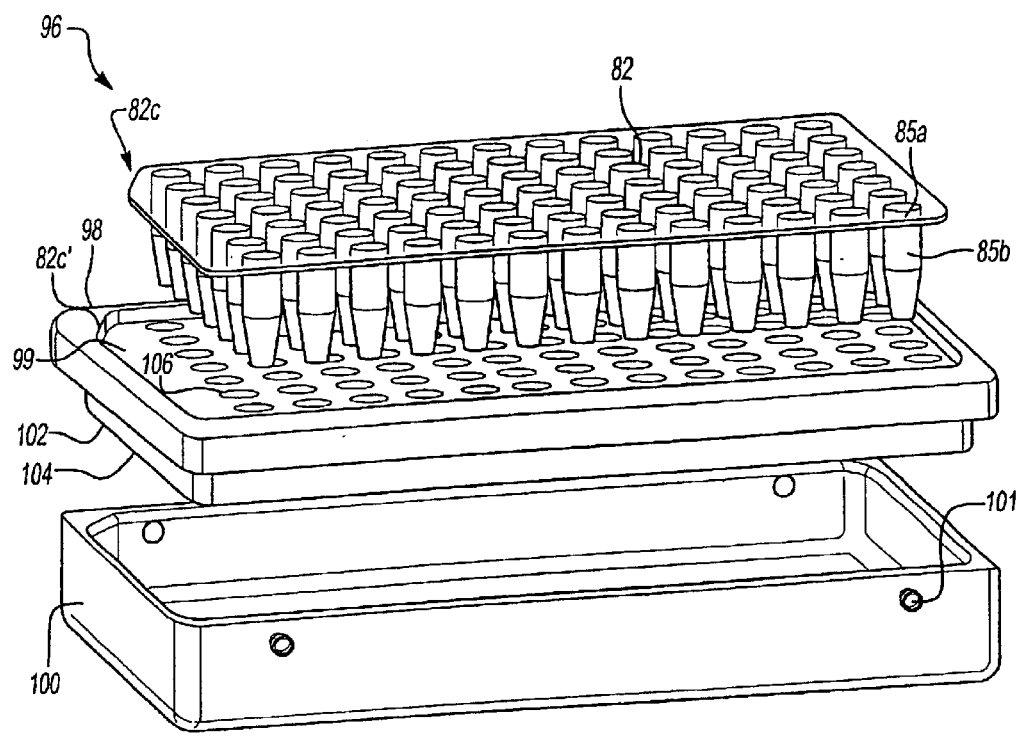
FIG. 14 is an exploded assembly view of the sled shown in FIG. 13.
Figure 15:
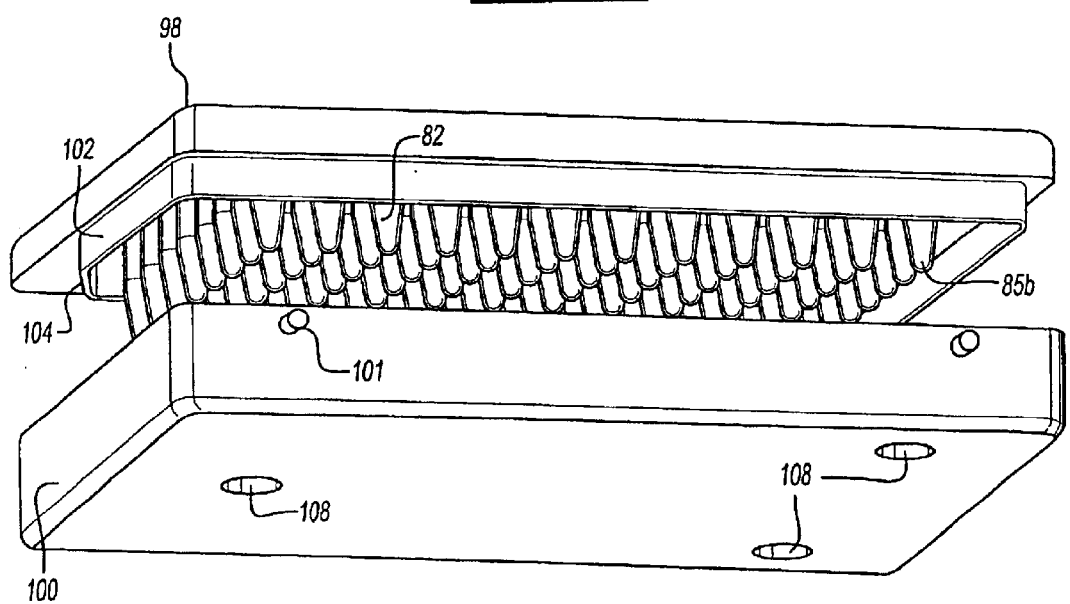
FIG. 15 is an exploded perspective view showing the bottom portion of the sled shown in FIG. 14.

Referring back to FIGS. 7a and 8, the carriage 66 may support a sled 96 for supporting a library of samples. As best seen in FIGS. 13–15, the sled 96 includes a removable top plate 98 and a bottom plate 100. One of skill in the art will appreciate that the sled 96 could be constructed as a unitary structure.

As shown in FIG. 13, the top plate 98 may be configured having a rectangularly shaped surface area defining an upper edge surrounding a recessed top surface 99. One of skill in the art will appreciate that the top plate 98 may be configured into other known geometric shapes, including, but not limited to circular, triangular, etc. As shown in FIG. 14, the inner surface of the top plate 98 may support a peripherally extending ridge 102 spaced inwardly a selected distance from the upper edge of the top plate 98. The ridge 102 defines a downwardly extending chamfered edge 104 surrounding the recessed top surface 99. The recessed top surface may include a plurality of openings 106, and the peripheral edges of the openings 106 may include a knife-edge (an edge having a thinner cross-section than the remainder of the top plate 98). This construction reduces the surface area of the top plate 98 that may contact portions of a sample support plate 82 (discussed below) received in the openings 106.

In the disclosed embodiment, the top plate 98 may be made of an insulating plastic in order to reduce heat transfer from the top plate 98 to the sample support plate 82, thus, reducing the amount of heat transferred from one sample to another. In the disclosed embodiment, the top plate 98 is fabricated of a polymer material, with the preferred material being Delrin®, available from DuPont. One of skill in the art will understand that Delrin® is a trademark identifying a polymer comprising an acetal resin. Delrin® is a highly versatile engineering plastic having metal-like properties. One of skill in the art would also understand that other materials having similar properties could be used.

As shown in FIG. 13, the bottom plate 100 receives and supports the top plate 98, and the bottom plate 100 is made of the material used to fabricate the top plate 98. As best seen in FIG. 13, the bottom plate 100 is configured having a rectangularly shaped surface area.

The bottom surface of the bottom plate 100 may also include one or more openings or registration pockets 108 in the bottom surface thereof. The registration pockets 108 may be filleted around the bottom peripheral edges to help facilitate repeatable registration with a mating part, even when the mating part is slightly out of alignment. Additionally, the sidewall portion of the bottom plate 100 may support indexing pins 101, which may be used to register the sled 96 to a mating part.

As best seen in FIG. 14, the sled 96 may support a sample support plate 82, wherein the sample support plate is in the form of a substrate and supports a library containing one or more material samples. As best seen in FIG. 14, the sample support plate 82 includes a plurality of wells 85a. Each well 85a includes an elongated, downwardly extending body portion 85b surrounding an open center, and the body portion 85b of each well 85a is received in a respective opening 106 of the top plate 98.

As shown in FIGS. 1 and 13–14, the sample plate 82 defines an array of adjacent wells 85a such that each well 85a is connected to an adjacent well 85a by an intermediate mass of material. It will also be appreciated, the wells can be individually formed and remain unconnected. The sample plate 82 may be fabricated in a variety of configurations using both simple and complex geometric shapes, including but not limited to circles, squares, rectangles, octagons, etc. Additionally, the sample plate 82 could comprise a flat plate having a plurality of depressions formed therein, wherein each depression is designed to support a liquid or solid sample. In one embodiment, the sample plate 82 may be a microtiter plate.

In the disclosed embodiment, the sample plate 82 is fabricated of a low thermal conductivity plastic material. More specifically, the sample plate 82 can be fabricated of a low thermal material that is compatible with IR thermography, wherein the preferred material is polypropylene. However, one of skill in the art will appreciate that other materials such as, but not limited to, metals, ceramics or other plastics could be used.

When the body portion 85b of the sample plate 82 is received in the openings 106, a very thin section of the top portion of the sample plate 82 contacts the top plate 98 at the knife-edge portion of openings 106. This type of arrangement helps reduce thermal cross-talk between the sample plate 82 and the top plate 98.

The sample plate 82 may also be registered to the top plate 98 in order to permit an operator to quickly discern incorrect orientation of the sample plate 82 relative to the top plate 98. For instance, in the disclosed embodiment, one corner of the top plate 98 includes a chamfer 82c' cut at an angle of approximately 45°. This chamfer 82c' aligns with a mating chamfer 82c formed on the sample plate 82, as best seen in FIG. 14.

Additionally, as best seen in FIG. 14, the sample plate 82 is received in the bottom plate 100 such that a gas filled gap may be formed between the sample plate 82 and the interior of the bottom plate 100. For instance, the sample plate 82 is indexed such that the sample plate 82 may be received in the bottom plate in only a single orientation. In the disclosed embodiment, the distance from the sample plate 82 to the walls of the bottom plate 100 has been maximized to allow the largest possible air gap without creating sufficient area for natural convection to take place. In the disclosed embodiment, the gas filled gap is less than or equal to approximately one centimeter. One of skill in the art will appreciate that the size of the gas filled gap may vary depending on the size of the sled 96 and the size and configuration of the sample plate 82.

Now referring to FIG. 16, the sled 96 may be configured as a room temperature block in order to provide a source for calibrating temperature sensitive external data gathering devices (discussed in detail below) that may be used in conjunction with the apparatus 10. One of skill in the art will appreciate that known calibration techniques may be employed to use the room temperature block.

In forming the room temperature block, the top plate 98 and sample plate 82 may be replaced by a mass having a high thermal conductivity. In the disclosed embodiment, the top plate 98 and the sample plate 82 are replaced by an aluminum block, the aluminum block preferably being fabricated from 6061-T6 grade aluminum. The aluminum block may be bead basted or polished to homogenize the surface. Additionally, the aluminum block may be black anodized and/or Teflon® sealed to help enhance radiative/emissive properties and corrosion resistance.

Figure 16:
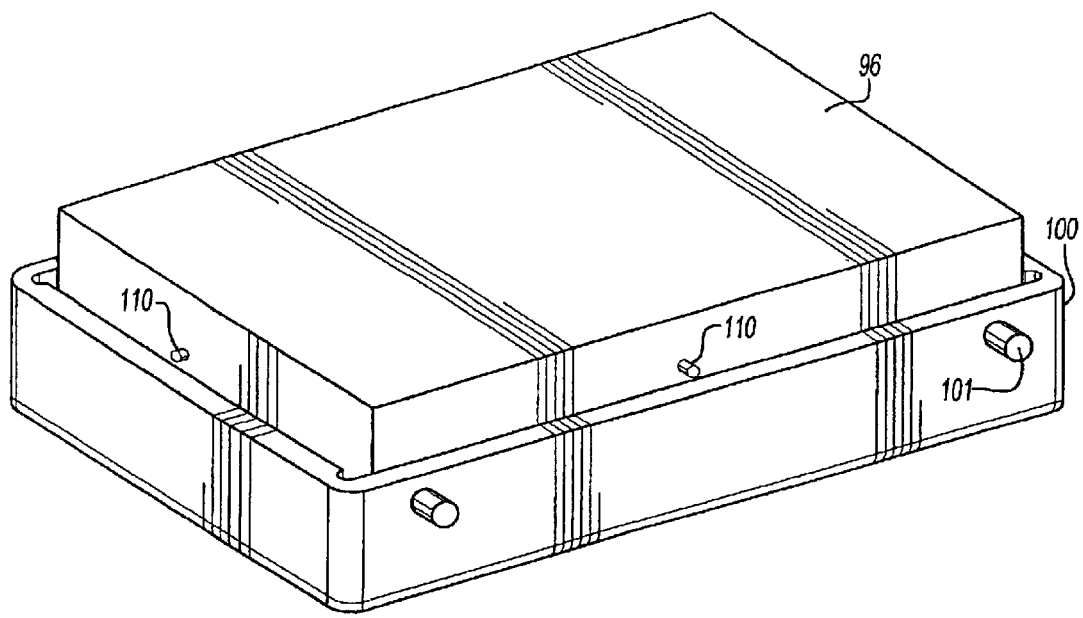
FIG. 16 shows an alternative embodiment of the sled shown in FIG. 13, wherein the sled has been configured as a room temperature block.

As shown in FIG. 16, the aluminum block is received in the open center of the bottom plate 100, and may include openings for receiving standoffs 110, said openings being located in the sidewall and bottom surface of the aluminum block. The standoffs 110 may be made of a material having a high thermal resisitivity to help isolate the aluminum block from temperature sinks or sources.

Figure 17:
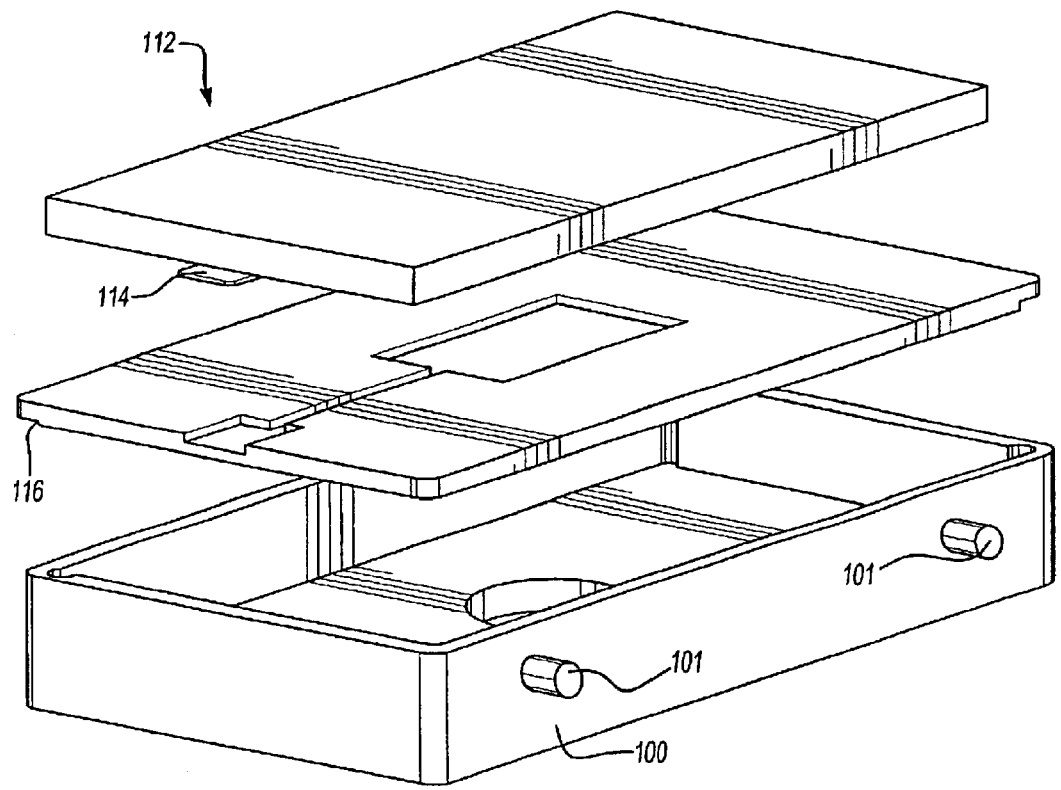
FIG. 17 shows another alternative embodiment of the sled shown in FIG. 13, wherein the sled has been configured as an elevated temperature block.

Referring to FIG. 17, the sled 96 may be configured as an elevated temperature block 112. Again, the elevated temperature block 112 may provide a device for calibrating temperature sensitive devices used in conjunction with the apparatus 10. Known techniques may be employed in using the elevated temperature block.

In forming the elevated temperature block 112, the top plate 98 and the sample plate 82 are replaced by a heater block 114. The heater block 114 is designed to permit homogeneous heating across its surface. Thus, the heater block 114 may be constructed of a material having high thermal conductivity. The top surface of the heater block 114 may be bead blasted or polished to homogenize the surface, and the entire heater block 114 may be black anodized and Teflon® sealed. However, any other polymer coating that enhances the corrosion resistance of the heater block 114 may be used.

As shown in FIG. 17, a flexible heating element may be coupled to the underside of the heater block 114. In the disclosed embodiment, a Kapton® substrate supporting a heating element, e.g., a resistive heater, is coupled to the heater block using a contact adhesive. Kapton® is a high-strength polyimide film available from DuPont. One of skill in the art will appreciate that other polyimide film or any other material that may support a resistive heating element could be used in place of the Kapton® polyimide film. Also, a thermocouple (not shown) may be coupled to the heater block 114 for temperature control purposes.

The opposite side of the Kapton® heater is coupled to an interface plate 116 using a contact adhesive. As shown in FIG. 17, the interface plate 116 is positioned between the heater block and the bottom plate 100, and defines a slot for receiving the Kapton® heater. The interface plate 116 may be made of a high thermal resistive material in order to help reduce heat transfer from the heater block 114 to adjacent external components.

Data Gathering Device 61

Referring now to FIGS. 6, 10 and 11, the screening apparatus 10 may be used in conjunction with data gathering device 61 in addition to a second data gathering device coupled to the electrical feed through 79 previously discussed. The data gathering device 61 may be any device capable of measuring and/or recording data determinative of one or more properties of the samples or one or more characteristics of reactions or interactions for each of the samples, individually or collectively, or in conjunction with other chemical components. Preferably, the data gathering device is an infrared sensitive camera assembly 61b, as best seen in FIGS. 6 and 11.

The IR camera assembly 61b is of a type known and used in the industry, and may include a camera head 65, a Dewar 61c for cooling components of the IR camera assembly 61b, and a focusing lens 61d. As best seen in FIG. 6, the IR camera head 65 is electrically coupled to the IR camera assembly 61b. Additionally, an IR camera filter wheel assembly 61e may be coupled to the IR camera assembly 61b above the IR focusing lens 61d using techniques known to one of skill in the art. If the IR camera is used as the data gathering device, it will be understood that the IR camera assembly 61b may be calibrated using known techniques. This calibration can take place using the temperature block 112 and/or the heater block 114 previously described.

As best seen in FIG. 6, the IR camera assembly 61b may be bolted to one end of a tube 130. And the opposite end of the tube 130 may be coupled to the upper end of the tube 60 via a retainer 62b bolted thereto. In this arrangement, the sapphire window 62a is sandwiched between the second tube 130 and the top end of the tube 60 and held in position by the retainer 62b.

Sealing the Reaction Chamber 48 and Coupling the Housing 12 to the Housing 64

To seal the reaction chamber 48, the opening 26 formed in the sidewall 18 must be sealed. As shown in FIG. 2, the opening 26 may be sealed by bringing the housing 64 into sealing engagement with the housing 12. Thus, when fully assembled, the reaction chamber 48 is enclosed by portions of the housing 12 and the housing 64.

As best seen in FIG. 1, the housing 64 may be coupled to the housing 12 by inserting a pair of guide rods 29 into openings 28 and 75 formed respectively in housings 12 and 64. As best seen in FIG. 4, one end of each guide rod 29 is received in a respective opening 28 of the housing 12 and the opposite end is received in a respective opening 75 defined by the front surface 69 of the housing 64. Additionally, the pneumatic cylinders 76 provide another means for coupling the housing 64 to the housing 12, and as previously described provide the power for moving the housing 64 into sealing contact with the housing 12.

Placement of Apparatus 10 into a Dry Box

Figure 12:
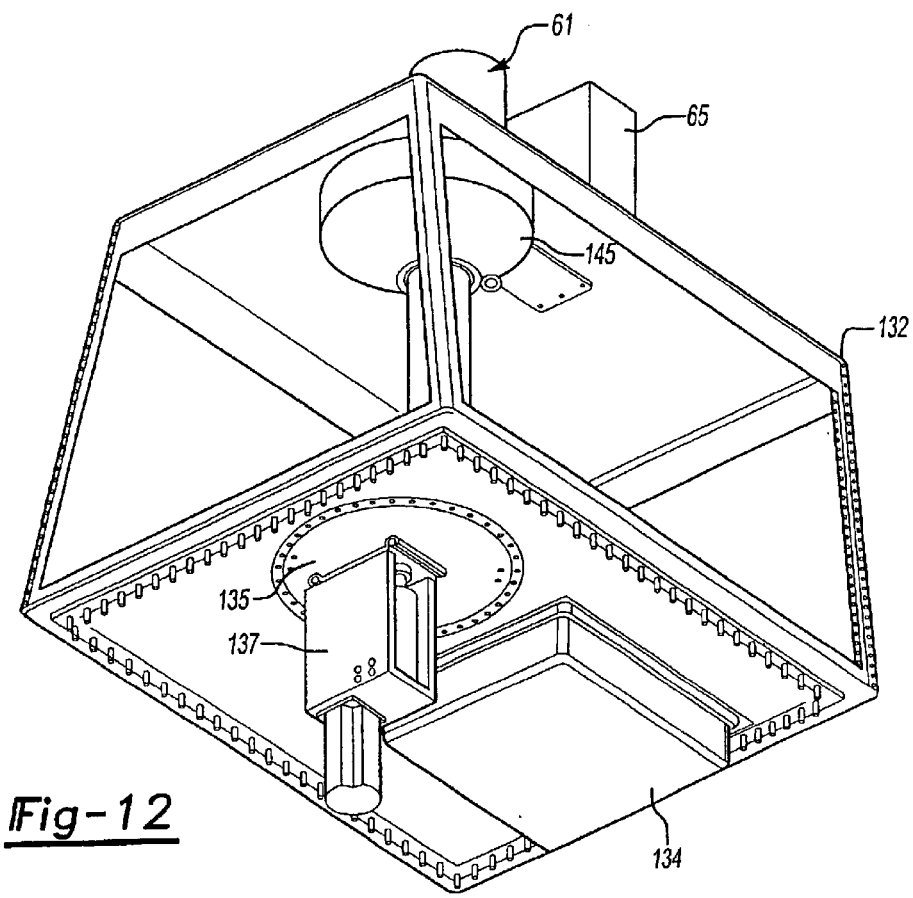
FIG. 12 is a bottom perspective view of the apparatus shown in FIG. 11.

The apparatus 10 may be enclosed in a dry box 132, as shown in FIGS. 11 and 12. Installation of the apparatus 10 in a dry box may allow the apparatus 10 to be used with chemicals or reactant components classified as hazardous or non-hazardous or water/oxygen sensitive chemicals, as the dry box 132 may isolate the apparatus 10 from the surrounding environment. As best seen in FIG. 6, when the apparatus is placed in the dry box 132, the data gathering device 61 in the form of the IR camera assembly 61b is coupled directly to the tube 130 camera mount 87 using threaded fasteners such as bolts or screws or other known techniques.

More specifically, as best seen in FIG. 11, the dry box 132 may include an opening 141 for permitting the camera mount 87 and other components to pass into the dry box 132. The opening 141 may be closed by a plate 145, wherein the plate 145 is attached to the dry box 132 using threaded fasteners such as bolts. In one embodiment, the opening 141 includes a diameter equal to that of the cover 22. This arrangement permits the IR camera assembly 61b to be positioned at various points along the perimeter of the opening 141. Preferably, the opening 141 and the plate 145 are configured to permit positioning of the IR camera assembly 61b in 60-degree increments around the perimeter of the opening 141.

Additionally, as best seen in FIGS. 11 and 12, the dry box 132 may include a removable floor 133 mounted to the sidewall surfaces of the dry box 132 using conventional pressure sealing and fastening techniques. Referring back to FIG. 12, the dry box 132 may further include a catch basin 134 supported by the removable floor 133 for providing storage for electrical or other components that are situated inside the dry box 132. The dry box 132 may also include a pressure relief mechanism or valve (not shown) such as a conventional burst disk to permit venting of the interior of the dry box 132 to ambient should the internal pressure of the dry box 132 exceed predetermined design limits.

As shown in FIGS. 6 and 12, the removable floor 133 of the dry box 132 may also include an opening 135 for receiving a motor mount 137, wherein the motor mount 137 is coupled to the housing 12. As best seen in FIG. 6, the motor mount 137 is coupled to a stepper motor 139 using known techniques, and the stepper motor 139 is coupled to the magnetic feed through 128 that drives the carousel 50.

Operation

Generally, when the reaction chamber 48 is sealed, the screening process can begin. However, prior to beginning the screening process, the reaction chamber 48 may be sealed and then pressurized with a charging agent. Alternatively, the reaction chamber 48 may be sealed and not pressurized or the reaction chamber 48 may not be sealed during a screening cycle. One method of operating the screening apparatus 10 will be discussed herein, wherein the reaction chamber 48 is sealed and pressurized by a charging agent.

The operation of the screening apparatus 10 may include the steps of (1) loading one or more libraries of samples into the reaction chamber 48, (2) sealing the reaction chamber 48, (3) introducing a charging agent into the sealed reaction chamber 48, (4) in-situ injection of chemical components into the reaction chamber 48, and (5) collecting data from two or more samples or libraries. These steps can be controlled by a computer or performed manually. Each of the aforementioned steps will be discussed in detail herein. However, one of skill in the art will appreciate that other methods may be used to operate the screening apparatus 10.

Loading a Library of Samples into the Reaction Chamber: Operation of the Transport Assembly 16.

As seen in FIG. 5a, a sled 96 retaining a library of samples on the sample plate 82 may be loaded into the reaction chamber 48 by the transport assembly 16. In the disclosed embodiment, the sled 96 and sample plate 82 may be manually placed onto the carriage 66, and the carriage 66 caused to move the sled 96 and sample plate 82 into the reaction chamber 48.

The carriage 66 is driven by activating the magnetic feed through threaded rod drive mechanism. As the motor turns, the magnetic feed through causes the threaded rod 74 to rotate clockwise, thus, moving the carriage 66 forward into the reaction chamber 48 through opening 26 of the housing 12.

The magnetic feed through is of a type conventionally used in the industry, and may include a magnetic driver assembly having one end coupled to the belt drive assembly (FIGS. 6–7) and the other end magnetically coupled to a magnetic follower. Rotation of the belt drive system induces a torque in the magnetic driver. Because of the magnetic coupling between the driver and the follower, rotation of the driver assembly induces rotation of the follower. The follower is coupled to the threaded rod 74 using generally known fastening and sealing techniques in order to maintain a pressure tight seal between the point of entry of the magnetic feed through into the housing 64. Hence, rotation of the follower results in rotation of the threaded rod 74, and as a result, the carriage 66, which is movably supported on the threaded rod 74, is caused to linearly traverse the threaded rod 74 when the magnetic feed through and belt drive are activated.

As best seen in FIG. 10, once the carriage 66 and sled 96 are inside the housing 12, the carriage 66 is brought to rest above the recessed surface 40 formed in the bottom surface 20 of the housing 12. After the sled 96 is in position, the carriage 66 is retracted, yet the sled 96 remains in the recess 40.

As shown in FIG. 10, the bellows 42 and the pneumatic cylinder 43 align directly below the recess 40. When the pneumatic cylinder 43 is extended, the bellows 42 contacts the sled 96, lifting the sled 96 out of the recess 40 and depositing the sled 96 in the slot 52.

When the sled 96 is received in the slot 52, the indexing pins 101 supported by the outer periphery of the sled 96 are received in the indents 53, thus securing the sled 96 in position in the slot 52 when the pneumatic cylinder 43, and hence the bellows 42, is retracted. Once the sled 96 is positioned in the slot 52, the sample plate 82 is visible through the open top of the slot 52.

Turning now to FIG. 5a, to position an empty slot 52 above the sled 96 located in the recess 40, the carousel 50 may be selectively rotated by the stepper motor 139 magnetic feed through 128 until an empty slot 52 is positioned above the sled 96. It will be appreciated that the structure of the magnetic feed through 128 is identical to that used to drive the carriage 66. Hence, a description of its operation will not be repeated here. One of skill in the art will appreciate that rotation of the carousel 50 may be manually or computer controlled.

To load a second sled 96 and sample plate 82 assembly into a respective slot 52, repeat the procedure described above until the desired number of slots 52 have been filled. To remove a sled 96 from a slot 52, the aforementioned process may be reversed.

Sealing the Reaction Chamber 48

Once the desired number of slots 52 has been filled, the housing 64 is caused to move into sealing engagement with the housing 12 by retracting the pneumatic cylinders 76. At this point, the reaction chamber 48 may be pressurized.

Introducing a Charging Agent into the Sealed Reaction Chamber

After sealing the reaction chamber 48, a charging agent may be introduced into the reaction chamber 48. In a preferred embodiment, the charging agent is a polymerizable gas that eventually becomes dissolved or absorbed into the respective samples comprising the library. Referring now to FIGS. 1 and 3a, the charging agent is introduced into the reaction chamber 48 through the inlet ports 30, 34 of the sidewall 18 and bottom surface 20 of the housing 12. The charging agent may be injected into the reaction chamber 48 such that homogenous mixing of the fluid takes place. The apparatus 10 may be configured to permit one or more charging agents to be introduced into the reaction chamber 48 simultaneously.

In the disclosed embodiment, the charging agent may be a gaseous monomer. More specifically, the charging agent may be ethylene gas introduced into the reaction chamber 48 under pressure. For instance, the gas could be introduced into the reaction chamber 48 at a pressure of approximately 60 PSI. One of skill in the art will appreciate that the other chemical components may be used as the charging agent, and that pressure levels may be used. For example, the reaction chamber 48 may be pressurized to 1 PSI, 5 PSI, 10 PSI, 50 PSI, 100 PSI, 200 PSI, 500 PSI, or 1000 PSI.

In-situ Injection of Chemical Components onto one or more Libraries

The in-situ injection of chemical components into the reaction chamber 48 may take place at any point or under any conditions prior to, during the course of, or after the screening. The process of in-situ injection can be computer controlled. For example, a computer can be programmed with software for controlling the sequence of the injections, as well as the timing for the injections.

Referring back to FIG. 1, to apply additional chemistry to a library, the transport assembly 16 is activated causing the carriage 66 to move into the housing 12 and a sled 96 supporting a sample plate 82 is removed from slot 52 in the manner previously described. The removal of the sled 96 from the slot 52 and the subsequent transportation of the sled 96 to the injection module 16 may occur without breaking the sealing contact between the housings 12, 64.

As illustrated in FIG. 18, the sled 96 may be moved incrementally under the injection manifold 80 such that desired injectors 89 of the injection manifold 80 align with selected samples supported by the sled 96. It will be appreciated that the injection manifold 80 is activated using conventional techniques to cause one or more chemical components to be applied to two or more samples retained on the sample plate 82.

Once the desired chemical components have been added to the library or selected samples of the library, the sled 96 is returned to the reaction re-inserted into the slot 52 from which it was removed. This aforementioned process may be repeated until all desired sample plates 82 have been treated with one or more chemical components and returned to the respective slot 52.

Collecting Data from one or more Libraries

Data gathering may commence once the desired chemical components or charging agents have been added to the samples. As best seen in FIG. 3b, to gather data concerning the samples under consideration, the carousel 50 is rotated so that a slot 52 supporting a library of samples is directly under the opening 46. As best seen in FIGS. 6 and 10, the opening 46 is directly below the sapphire window 62a (FIG. 10) and the line of sight of the IR camera assembly 61b. Thus, the infrared camera 61b, when activated, may collect digital images (e.g., photographs) of the library through the sapphire window 62a, recording exothermic/endothermic reactions at each of the samples. Hence, the camera 61b detects and records the intensity of infrared radiation passing through the sapphire window 62a.

The operation of the infrared camera 61b may be manually or computer controlled. In the disclosed embodiment, the operation of the infrared camera 61b is controlled by a computer programmed with specific instructions for controlling the frequency and duration at which the digital images are taken over a given time period. The computer software also coordinates and synchronizes the picture taking activity of the camera 61b with the rotation of the carousel 50 to align a slot 52 below the opening 46.

In an alternative embodiment, data may be gathered by coupling appropriate electrical components or probes to one or more samples supported by each sample support plate 82 via the electrical feed through 79. For example, data characterizing thermal characteristics of reaction or other material properties may be measured by coupling a thermister or thermocouple to the sample plate 82 at each of the sample wells or the individual samples themselves via the electrical feed through 79. Again, the collection of data via the electrical feed through 79 may be performed manually or by and appropriately programmed computer.

After the data gathering process has been completed, the system may be evacuated, purged, and the process described herein repeated.

ILLUSTRATIVE EXAMPLES

These examples illustrate only a few of the many ways in which the apparatus 10 could be used in practice, and are not intended to limit the manner in which the apparatus 10 could be used by one of skill in the art.

General Set-up Instructions

FIG. 11 shows the set-up of an apparatus that could be used to conduct the experiment set forth in these illustrative examples. Also, in the embodiment of the apparatus 10 used to perform the illustrative examples, the major functions of the apparatus 10 are computer controlled. For instance, the operation of the transport assembly 16, venting the reaction chamber 48, the movement of the injection module 14, the process of in-situ injection of chemical components into the reaction chamber 48, loading/unloading and rotation of carousel 50 and the process of gathering data using an IR camera are all computer controlled. Additionally, the inlet ports 34 of the apparatus are coupled to a source of gas that serves as the charging agent. The libraries to be examined are loaded into the housing 12 using the techniques previously described for the apparatus 10.

All manipulations were performed in an inert atmosphere glove box containing argon or nitrogen using standard techniques for the handling of air sensitive materials as described in Shriver, D. F.; Drezdzon, M. A. *The Manipulation of Air-Sensitive Compounds*, 2 ed.; John Wiley & Sons, Inc.: New York, 1986. Toluene and hexane were purified according to procedures described in Grubbs, R. H. et al "Safe and Convenient Procedure for Solvent Purification", *Organometallics* 1996, 15, 1518–20. Reagents were purified according to procedures described in Armarego, W. L. F.; Perrin, D. D. *Purification of Laboratory Chemicals*, $4^{th}$ ed.; Butterworth and Heinemann: Oxford, UK, 1996. CP Grade ethylene was purchased from Matheson, Inc. (6775 Central Avenue, Newark, Calif. 94560) and was further purified by passing it through a Matheson Model 6427-4S Oxygen/Moisture drying tube before use. $Ni(acac)_2$ (acac=acetylacetonate) was purchased from Strem Chemicals, Inc. (7 Mulliken Way, Dexter Industrial Park, Newburyport, Mass. 01950) and used without further purification, and $(py)_2Ni(CH_2SiMe_3)_2$ (py=pyridine) was prepared according to the method described in Carmona, E.; Gonzalez, F.; Poveda, M.; Atwood, J. L.; Rogers, R. D. *J. C. S. Dalton Trans.*, 1981, 777–782. Triisobutylaluminum was purchased from the Aldrich Chemical Company, Inc. (1001 West Saint Paul Avenue, Milwaukee, Wis. 53233) and tris(pentafluorophenyl)boron was purchased from Strem; both were used without further purification. $Me_2$-DAB-$Mes_2$ stands for N,N'-(2,4,6-trimethylphenyl)-2,3-diiminobutane and was prepared as described in Johnson, L. K.; Killian, C. K.; Brookhart, M. B. *J. Am. Chem. Soc.*, 1995, 117, 6414–6415 (and references cited therein). Commercially available 96-well polypropylene microtiter plates were used to contain the libraries of catalysts screened in the examples below.

Example 1

Infrared Thermography Screening of a Single 96-Well Ligand Library

The following example illustrates the use of the invention for activation of a single library under pressure and temperature equilibrium with two different chemical components (activators) using the in-situ injection system.

To a 96-element polypropylene library containing different ligands was added 60 $\mu$L/well of a $5.0\times10^{-3}$ M toluene solution of $Ni(acac)_2$ using a multichannel pipettor. The contents of the wells within the library were then shaken for 45 minutes. The library was loaded onto the carousel within the reaction chamber using the transport assembly. The reaction chamber was pressurized to 60 PSI with ethylene gas and allowed to undergo pressure and temperature equilibrium over a period of 10 minutes. Using the transport assembly the library was then moved from the carousel to the in-situ injector within the apparatus. Using the injectors, 15 $\mu$L of a $1.0\times10^{-1}$ M solution of triisobutylaluminum in toluene was added to each well in the library. The library was allowed to stand for 3 minutes and then using the injectors 60 $\mu$L of a $1.0\times10^{-2}$ M toluene solution of tris(pentafluorophenyl)borane was added to each well in the library. Using the transport assembly the library was then returned to the carousel such that it was directly in view of the infrared camera and was monitored for catalyst activity over a period of 1 hour by infrared thermography. At the completion of the experiment, the apparatus was depressurized automatically, purged with nitrogen for 10 minutes, and the library was removed from the carousel using the transport assembly and subsequently removed from the apparatus.

Example 2

Infrared Thermography Screening of Six 96-Well Ligand Libraries

The following example illustrates the use of the apparatus for activation of six libraries under pressure and temperature equilibrium with a single chemical component (activator) using the in-situ injection system.

The metal precursor, $(Me_2—DAB—Mes_2)Ni(CH_2SiMe_3)_2$, used in this example was prepared as follows: To a 40 mL glass vial was added 196 mg (0.50 mmol) of $(py)Ni(CH_2SiMe_3)_2$ and 160 mg (0.50 mmol) of $Me_2—DAB—Mes_2$ followed by 8 mL of hexane. The reaction mixture was stirred for 1.5 h at RT and eventually became dark blue-green in color. The volatiles were then removed in vacuo and the resulting dark blue-green crystalline solids were washed with hexane and dried in vacuo. The product was identified on the basis of its $^1H$ NMR spectrum and used without further purification.

Into selected wells of six, 96-well libraries were added 60 $\mu$L aliquots of a $5.0\times10^{-3}$ M toluene solution of $(Me_2—DAB—Mes_2)Ni(CH_2SiMe_3)_2$ using a pipettor. The libraries were then loaded onto the carousel within the reaction chamber using the transport assembly. The reaction chamber was pressurized to 60 PSI with ethylene gas and allowed to undergo pressure and temperature equilibrium over a period of 10 minutes. Using the transport assembly the library was then moved from the carousel to the in-situ injection module within the apparatus. Using the injectors 60 $\mu$L of a $1.0\times10^{-2}$ M toluene solution of tris(pentafluorophenyl)borane was added to each well of each library. The libraries were then alternatively rotated on the carousel into direct view of the infrared camera which monitored catalyst activity by infrared thermography over a period of 1 hour. At the completion of the experiment, the apparatus was depressurized automatically, purged with nitrogen for 10 minutes, and the libraries were removed from the carousel using the transport assembly and subsequently removed from the apparatus.

Alternative Embodiment of Apparatus 10

In an alternative embodiment of the apparatus 10, the injection module 14 can be mounted directly onto the housing 12, thus eliminating housing 64. In this embodiment, the housing 12 could be formed as a completely enclosed member, wherein the samples are manually loaded before the cover 22 is attached.

In a second alternative embodiment, the injection module 14 could be supported by the housing 12, and the housing 12 sealed by a surface (not shown) brought into sealing engagement with the front surface 24. In this embodiment, the distance the transport module 16 transports the sample plates 82 within the reaction chamber 48 or between the reaction chamber 48 and the housing 12 may be significantly reduced.

In a third alternative embodiment, the apparatus 10 may be adapted to include a mechanism or means for agitating the samples either individually or collectively. For instance, the apparatus 10 may include a stirring assembly of the type disclosed in co-pending U.S. application Ser. No. 09/826,606, entitled Parallel Reactor for Sampling and Conducting In-Situ Flow-Through Reactions and a Method of Using Same, incorporated herein by reference. Alternatively, agitation may be introduced into the samples by other means or techniques, including, but not limited to, vibratory devices, electromechanical/electromagnetic instruments or other similar devices or instruments for stimulating the samples at a molecular or particle level.

Additionally, the agitation mechanism or means may be used in conjunction with an apparatus for heating or cooling the samples either individually or collectively. For instance, one or more samples, or alternatively two or more samples, may be exposed to an apparatus that permits heat transfer to or from the respective samples via conduction, convection or radiative processes or techniques.

Preferred embodiments of the present invention have been disclosed. A person of ordinary skill in the art would realize, however, that certain modifications would come within the teachings of this invention. Therefore, the following claims should be studied to determine the true scope and content of the invention.

What is claimed is:

1. An apparatus for injection of one or more chemical components into a reaction chamber, comprising:
   a reaction chamber for receiving one or more libraries, each of the libraries comprising two or more samples, the reaction chamber configured to form a sealed enclosure; and
   an injection manifold supporting injectors for injection of one or more chemical components onto respective samples of the one or more libraries with the sealed reaction chamber pressurized;
   wherein material and structure of the reaction chamber is such that the sealed enclosure can withstand a pressure of approximately 5 psi.

2. The apparatus of claim 1 wherein the material and structure of the sealed reaction chamber is such that the reaction chamber can withstand a pressure of approximately 60 psi.

3. The apparatus of claim 1 wherein the reaction chamber further comprises at least one inlet port for receiving a charging agent.

4. The apparatus of claim 1 further comprising a pressure gauge for measuring the pressure of the reaction chamber.

5. The apparatus of claim 1 wherein the injection manifold permits in-situ injection of said one or more chemical components onto respective samples in the sealed reaction chamber.

6. The apparatus of claim 1 further comprising a heating system for heating the samples.

7. The apparatus of claim 1 wherein the injectors are adapted to apply the chemical components directly to the respective samples comprising the one or more libraries.

8. The apparatus of claim 1 wherein the respective injectors are in fluid communication with at least one pump for delivering one or more of said chemical components to the respective injectors.

9. The apparatus of claim 1 further comprising one or more control valves for venting or controlling the pressure of the reaction chamber.

10. The apparatus of claim 1 wherein said samples are retained on a sample plate.

11. The apparatus of claim 10 wherein the sample plate is a microtiter plate.

12. The apparatus of claim 1 wherein the one or more libraries comprise two or more materials on a common substrate or in separate vials supported on a common substrate.

13. The apparatus of claim 1 further comprising a stirring system for agitating the samples.

14. The apparatus of claim 13 wherein the stirring system comprises magnetic stirrers.

15. The apparatus of claim 1 further comprising a transport assembly configured to transport one or more components within the reaction chamber.

16. The apparatus of claim 1 wherein the injection manifold is supported by a housing.

17. The apparatus of claim 16 wherein the housing defines at least a portion of the reaction chamber.

18. The apparatus of claim 1 further comprising an evacuation port configured for connection to a vacuum source for evacuating or purging the reaction chamber.

19. A method for injection of one or more chemical components into a reaction chamber, comprising:
   inserting one or more libraries into a reaction chamber, each of the libraries comprising two or more samples;
   sealing the reaction chamber;
   pressurizing the reaction chamber; and
   injecting one or more chemical components onto respective samples of the one or more libraries with the sealed reaction chamber pressurized.

20. The method of claim 19 further comprising allowing the reaction chamber to reach a specified temperature before injecting said one or more chemical components.

21. The method of claim 19 further comprising allowing the reaction chamber to reach pressure and temperature equilibrium before injecting said one or more chemical components.

22. The method of claim 19 wherein pressurizing the sealed reaction chamber comprises pressurizing the chamber to a pressure of approximately 5 psi.

23. The method of claim 19 wherein pressurizing the sealed reaction chamber comprises pressurizing the chamber to a pressure of approximately 60 psi.

24. The method of claim 19 further comprising heating the samples.

25. The method of claim 19 further comprising stirring the samples.

26. The method of claim 25 wherein stirring the samples comprises stirring the samples with magnetic stirrers.

27. The method of claim 19 further comprising evacuating or purging the reaction chamber.

28. The method of claim 19 each of the one or more libraries comprises two or more materials on a common substrate or in separate vials supported on a common substrate.

29. The method of claim 28 wherein the common substrate is a microtiter plate.

30. The method of claim 19 wherein the chemical components are injected onto two or more samples.

31. The method of claim 19 further comprising transporting one or more components within the reaction chamber while the reaction chamber is pressurized.

32. The method of claim 19 wherein pressurizing the reaction chamber comprises introducing a charging agent into the reaction chamber.

33. The method of claim 19 wherein the chemical components may be injected onto the samples without increasing or decreasing the pressure of the reaction chamber.

34. An apparatus for injection of one or more chemical components into a reaction chamber, comprising:

a reaction chamber for receiving one or more libraries, each of the libraries comprising two or more samples, the reaction chamber configured to form a sealed enclosure;

an injection manifold supporting injectors for injection of one or more chemical components onto respective samples of the one or more libraries with the sealed reaction chamber pressurized; and an inlet port in fluid communication with the reaction chamber for supplying pressurized fluid to the reaction chamber;

wherein the sealed enclosure formed by the reaction chamber is configured to sustain pressure during injection of the one or more chemical components onto the respective samples of the one or more libraries.

35. The apparatus of claim 34 wherein the reaction chamber is pressurized by a charging agent.

36. The apparatus of claim 34 further comprising a pressure gauge for measuring the pressure of the reaction chamber.

* * * * *